United States Patent
Mizusaki et al.

(10) Patent No.: US 10,059,881 B2
(45) Date of Patent: Aug. 28, 2018

(54) MONOMER, LIQUID CRYSTAL COMPOSITION, LIQUID CRYSTAL DISPLAY DEVICE, AND PRODUCTION METHOD FOR LIQUID CRYSTAL DISPLAY DEVICE

(71) Applicants: Sharp Kabushiki Kaisha, Osaka-shi, Osaka (JP); Toyo Gosei Co., Ltd., Ichikawa-shi, Chiba (JP)

(72) Inventors: Masanobu Mizusaki, Osaka (JP); Youhei Nakanishi, Osaka (JP); Takeshi Noma, Osaka (JP); Satoshi Enomoto, Inzai (JP)

(73) Assignees: SHARP KABUSHIKI KAISHA, Sakai (JP); TOYO GOSEI CO., LTD., Chiba (JP)

( * ) Notice: Subject to any disclaimer, the term of this patent is extended or adjusted under 35 U.S.C. 154(b) by 0 days.

(21) Appl. No.: 14/436,532

(22) PCT Filed: Oct. 17, 2013

(86) PCT No.: PCT/JP2013/078237
§ 371 (c)(1),
(2) Date: Apr. 17, 2015

(87) PCT Pub. No.: WO2014/061756
PCT Pub. Date: Apr. 24, 2014

(65) Prior Publication Data
US 2016/0168465 A1    Jun. 16, 2016

(30) Foreign Application Priority Data
Oct. 19, 2012    (JP) ................................. 2012-232327

(51) Int. Cl.
C09K 19/56 (2006.01)
C09K 19/20 (2006.01)
(Continued)

(52) U.S. Cl.
CPC ............ *C09K 19/56* (2013.01); *C07C 69/602* (2013.01); *C07C 233/27* (2013.01);
(Continued)

(58) Field of Classification Search
CPC .............................................. C09K 2019/0448
See application file for complete search history.

(56) References Cited

U.S. PATENT DOCUMENTS

2005/0074692 A1* 4/2005 Makino ................. B41C 1/1016
430/270.1
2005/0116200 A1    6/2005 Nakanishi et al.
(Continued)

FOREIGN PATENT DOCUMENTS

CN    101556404 A * 4/2011
JP    06-211758 A    8/1994
(Continued)

OTHER PUBLICATIONS

Official Communication issued in International Patent Application No. PCT/JP2013/078237, dated Jan. 14, 2014.

*Primary Examiner* — Chanceity N Robinson
(74) *Attorney, Agent, or Firm* — Keating & Bennett, LLP

(57) ABSTRACT

An aspect of the present invention provides a monomer from which a polymer layer capable of keeping high display quality even in high temperature and high humidity environments can be formed. The monomer in an aspect of the present invention is a compound represented by P-$Sp^1$-$Z^2$-$A^1$-$(Z^1$-$A^2)_{n1}$-$Z^3$-$Sp^2$-P: in the formula, P denotes the same or different radical polymerizable group; and at least one of $Z^1$, $Z^2$, and $Z^3$ denotes —NRCO— or —CONR— group.

24 Claims, 2 Drawing Sheets

(51) Int. Cl.
  *C09K 19/52*      (2006.01)
  *C08F 22/36*      (2006.01)
  *C08F 222/36*     (2006.01)
  *C07C 69/602*     (2006.01)
  *C07C 233/55*     (2006.01)
  *G02F 1/1337*     (2006.01)
  *C07C 233/27*     (2006.01)
  *C09K 19/04*      (2006.01)
  *C08F 222/10*     (2006.01)
  *G02F 1/1341*     (2006.01)

(52) U.S. Cl.
  CPC ............ *C07C 233/55* (2013.01); *C08F 22/36* (2013.01); *C08F 222/36* (2013.01); *C09K 19/20* (2013.01); *C09K 19/52* (2013.01); *G02F 1/133788* (2013.01); *C08F 2222/102* (2013.01); *C09K 2019/0448* (2013.01); *G02F 1/1341* (2013.01); *G02F 1/133711* (2013.01)

(56) References Cited

U.S. PATENT DOCUMENTS

| | | | | |
|---|---|---|---|---|
| 2011/0102720 | A1* | 5/2011 | Mizusaki | C08F 20/00 349/123 |
| 2011/0267574 | A1* | 11/2011 | Kawahira | G02F 1/133788 349/158 |
| 2013/0169916 | A1* | 7/2013 | Mizusaki | C09K 19/14 349/123 |
| 2013/0342791 | A1* | 12/2013 | Mizusaki | C09K 19/14 349/86 |
| 2014/0168586 | A1 | 6/2014 | Mizusaki et al. | |

FOREIGN PATENT DOCUMENTS

| | | |
|---|---|---|
| JP | 2003-307720 A | 10/2003 |
| WO | 2009/157207 A1 | 12/2009 |
| WO | 2012/032857 A1 | 3/2012 |
| WO | 2012/121319 A1 | 9/2012 |

\* cited by examiner

MONOMER, LIQUID CRYSTAL COMPOSITION, LIQUID CRYSTAL DISPLAY DEVICE, AND PRODUCTION METHOD FOR LIQUID CRYSTAL DISPLAY DEVICE

TECHNICAL FIELD

An aspect of the present invention relates to a liquid crystal composition, a liquid crystal display device, and a production method for a liquid crystal display device. More particularly, an aspect of the present invention relates to a liquid crystal composition for forming a polymer layer by which orientation of liquid crystal molecules can be controlled, a liquid crystal display device having a polymer layer which can control orientation of liquid crystal molecules and which is formed by polymerizing a monomer contained in a liquid crystal composition (hereinafter, also referred to as polymer sustained alignment (PSA) layer, a production method preferable for producing the liquid crystal display device and the like.

BACKGROUND ART

A liquid crystal display (LCD) device is an appliance capable of controlling transmission/blocking of light (on/off of display) by controlling alignment of liquid crystal molecules having birefringence. A liquid crystal display device has, for example, an array substrate, a color filter substrate, and a liquid crystal layer sandwiched between a pair of substrates, that is, the color filter substrate and the array substrate. The surfaces of both substrates in the liquid crystal layer side may have an alignment film, each.

Hereinafter, one example of production steps for a liquid crystal display device will be described. A plurality of spacers made of an insulating material are formed on one of the above-mentioned substrates and both substrates are stuck to each other. In the case of employing an ODF (one-drop-fill) method, a liquid crystal material is dropped before sticking the substrates, and in the case of employing a vacuum injection method, a liquid crystal material is vacuum-injected after the substrates are stuck and the inject is closed. Thereafter, a polarizing plate and a phase difference film are stuck to the faces of the respective substrates in the reverse sides of the liquid crystal layer to complete a liquid crystal display panel. Further, a gate driver, a source driver, a display control circuit, etc. are mounted on the liquid crystal display panel and a back light unit or the like is combined to complete a liquid crystal display device.

In recent years, a technique for forming a polymer layer (PSA layer) capable of controlling orientation of liquid crystal molecules on an alignment film or on a substrate having no alignment film has drawn attention. A PSA layer is formed by sealing a liquid crystal composition obtained by mixing a polymerizable component such as a monomer, an oligomer, or the like with a liquid crystal material between substrates and polymerizing the polymerizable component by heat or light (e.g. ultraviolet) irradiation.

Patent document 1 discloses formation of an alignment retention layer by sandwiching, between both substrates bearing a photo-alignment film, a liquid crystal material obtained by mixing a photo-polymerizable compound, and polymerizing the photo-polymerizable compound by light irradiation. The photo-alignment film disclosed in Patent Document 1 is an alignment film containing a polymer having a main chain and a side chain including a photo-reactive functional group, and a plurality of regions for providing alignment regulation force in different directions for the alignment film are formed by irradiating the alignment film with light from different directions. Owing to the light irradiation, an impurity is sometimes generated from the photo-alignment film, but the impurity is immobilized by the alignment retention layer and generation of impurity ions in the liquid crystal layer is suppressed to fix the pre-tilt direction of liquid crystal molecules and at the same time to suppress decrease of voltage holding ratio and occurrence of image sticking.

Patent Document 2 discloses that image sticking of a liquid crystal display device can be lessened by injection of a liquid crystal composition containing a polymerizable monomer between substrates and irradiating with ultraviolet rays while applying voltage between transparent electrodes on the opposite to each other on the substrates to polymerize the monomer and that the monomer has one or more ring structures or condensed ring structure, and 2 functional groups directly bonded to the ring structure or the condensed ring structure.

CITATION LIST

Patent Literature

Patent Literature 1: WO 2009/157207
Patent Literature 2: JP 2003-307720 A

SUMMARY OF INVENTION

Technical Problem

When a liquid crystal display device which is subjected to PSA treatment is used in high temperature and high humidity environments for a long time, stains and display unevenness may sometimes occur along the outer rim of a display region. Occurrence of stains and display unevenness will be described below. When a liquid crystal display device is used in high temperature and high humidity environments for a long time, a region where stains are generated along the outer rim of the display region of the liquid crystal display device appears and brightness differs between the outer rim of the display region and the center part, and thus display unevenness is sometimes observed. The display region means a region for displaying images which an observer recognizes, and excludes a picture-frame region. A gate driver, a source driver, a display control circuit, etc. are installed in the picture-frame region.

In recent years, regarding a liquid crystal display device, the display region tends to be widened and it is required to narrow the picture-frame region. If the picture-frame region is narrowed, as described above, the region where stains and display unevenness occur becomes noticeable and the display quality of a liquid crystal display device is considerably lowered.

Some aspects of the present invention are completed in view of the above state of the art and it is an object in an aspect of the present invention to provide a monomer and a liquid crystal composition capable of forming a polymer layer for maintaining high display quality even in high temperature and high humidity environments, a liquid crystal display device capable of maintaining high display quality even in high temperature and high humidity environments, and a production method for a liquid crystal display device capable of maintaining high display quality even in high temperature and high humidity environments.

Solution to Problem

The present inventors have made investigations on the cause of occurrence of stains and display unevenness in a liquid crystal display device and paid attention to a step of sticking both substrates by using a sealing material in the liquid crystal display device production process. Based on the results of various investigations, the inventors consequently found that water attributed to moisture or the like penetrates the liquid crystal display device from outside when a liquid crystal display device is used in high temperature and high humidity environments and that a component of the sealing material is sometimes eluted together with the water to the liquid crystal layer. Further, the inventors found that existence of these water and impurities in a liquid crystal layer generates stains and display unevenness.

The inventors have made further investigations and finally found that alignment of liquid crystal molecules could be controlled and generation of stains and display unevenness could be prevented even in the case of use in high temperature and high humidity environments by sandwiching, between both substrates, a liquid crystal composition containing a liquid crystal material and a radical polymerizable monomer having an amide group, and forming a polymer layer (PSA layer) by polymerizing the monomer by ultraviolet irradiation.

Hereinafter, the reason for suppressing generation of stains and display unevenness in a liquid crystal display device will be described.

A conventional monomer to be used for forming a polymer layer (PSA layer) has an ester group (—COO— group). Since having relatively high polarity, —CO— in the ester group causes dipole-dipole interaction with another polar molecule (e.g. water molecule, those with high polarity among components derived from a sealing material, etc.). However, in high temperature and high humidity environments, it becomes difficult for a conventional monomer to keep interaction with water or impurities derived from a sealing material and thus the impurities or the like remain in the liquid crystal layer.

On the other hand, since having extremely high polarity as compared with that in the case of an ester, —CO— in the amide group (—NRCO— group) of the radical polymerizable monomer in an aspect of the present invention causes extremely strong dipole-dipole interaction with another polar molecule. Further, the amide group (—NHCO—) has a nitrogen atom and is capable of forming a hydrogen bond with a polar molecule having hydrogen affinity such as water through the hydrogen atom bonded to the nitrogen atom. Accordingly, since a radical polymerizable monomer having an amide group can have strong interaction with an impurity with high polarity, particularly with an impurity having hydrogen affinity, the radical polymerizable monomer can take in water and an impurity with high polarity even in high temperature and high humidity environments and can prevent remaining of the impurity in the liquid crystal.

As a result, the inventors of the present invention can solve the above-mentioned problem and these findings have now led to completion in an aspect of the present invention.

A monomer in an aspect of the present invention is a compound represented by the following chemical formula (1).

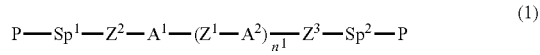

(1)

In the formula,

P denotes the same or different radical polymerizable group;

$Sp^1$ and $Sp^2$ may be the same or different, and respectively denote a straight or branched alkylene or alkyleneoxy group with 1 to 6 carbon atoms, or a direct bond;

$A^1$ denotes a divalent alicyclic, aromatic monocyclic, or condensed polycyclic hydrocarbon group;

$A^2$ denotes a phenylene group;

a —$CH_2$— group included in $A^1$ and $A^2$ may be substituted with an —O— or a —S— group unless neighboring each other;

a —CH= group included in $A^1$ and $A^2$ may be substituted with a —N= group unless neighboring each other;

a hydrogen atom included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^1$, $Z^2$, and $Z^3$ may be the same or different and denote —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —NRCO—, —CONR—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH=CH—, —CF=CF—, —C≡C—, —CH=CH—COO—, —OCO—CH=CH— groups, or a direct bond;

at least one of $Z^1$, $Z^2$, and $Z^3$ denotes —NRCO— or —CONR— group;

R denotes a hydrogen atom, or a straight alkyl or alkenyl with 1 to 6 carbon atoms; and $n^1$ denotes 0 or 1.

A liquid crystal composition in an aspect of the present invention contains the above-mentioned monomer as a constituent element.

In consideration of low solubility of a monomer having an amide group in a liquid crystal, a compound represented by the above-mentioned formula (1) is preferable to have an introduced modification group such as a straight alkyl or alkenyl group with 1 to 6 carbon atoms. These introduced modification group enables the monomer having an amide group to improve solubility in the liquid crystal.

Examples of $A^1$ included in a compound represented by the above-mentioned formula (1) may include benzene-1,2-diyl, benzene-1,3-diyl, benzene-1,4-diyl, pyridine-2,3-diyl, pyridine-2,4-tolyl, pyridine-2,5-diyl, pyridine-2,6-diyl, naphthalene-1,2-diyl, naphthalene-1,4-diyl, naphthalene-1,5-diyl, naphthalene-1,8-diyl, naphthalene-2,3-diyl, naphthalene-2,6-diyl, naphthalene-2,7-diyl, cyclohexane-1,2-diyl, cyclohexane-1,3-diyl, cyclohexane-1,4-diyl, decahydronaphthalene-1,2-diyl, decahydronaphthalene-1,4-diyl, decahydronaphthalene-1,5-diyl, decahydronaphthalene-1,8-diyl, decahydronaphthalene-2,3-diyl, decahydronaphthalene-2,6-diyl, indane-1,1-diyl, indane-1,3-diyl, indane-1,5-diyl, indane-1,6-diyl, phenanthrene-1,6-diyl, phenanthrene-1,8-diyl, phenanthrene-1,9-diyl, phenanthrene-2,7-diyl, phenanthrene-2,9-diyl, phenanthrene-3,6-diyl, phenanthrene-3,9-diyl, phenanthrene-9,10-diyl, anthracene-1,4-diyl, anthracene-1,5-diyl, anthracene-1,9-diyl, anthracene-2,3-diyl, anthracene-2,6-diyl, anthracene-2,9-diyl, and anthracene-9,10-diyl group, and examples of $A^2$ may include benzene-1,2-diyl, benzene-1,3-diyl, and benzene-1,4-diyl group.

Examples of a compound represented by the above-mentioned formula (1) may include compounds represented by the following chemical formula (2).

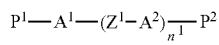
(2)

In the formula, $A^1$ denotes a divalent alicyclic, aromatic monocyclic, or condensed polycyclic hydrocarbon group;

$A^2$ denotes a phenylene group;

a —$CH_2$— group included in $A^1$ and $A^2$ may be substituted with an —O— or a —S— group unless neighboring each other;

a —$CH_2$= group included in $A^1$ and $A^2$ may be substituted with a —N= group unless neighboring each other;

a hydrogen atom included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^1$ denotes —O—, —CO—, —COO—, —OCO—, —NRCO—, —CONR— groups, or a direct bond;

R denotes a hydrogen atom, or a straight alkyl or alkenyl group with 1 to 6 carbon atoms;

$P^1$ and $P^2$ may be the same or different and denote a radical polymerizable group and at least one of $P^1$ and $P^2$ is an acryloylamino or a methacryloylamino group; and $n^1$ denotes 0 or 1.

More practical examples of a compound represented by the above-mentioned formula (1) may include compounds represented by one of the following formulas (5-1) to (5-18).

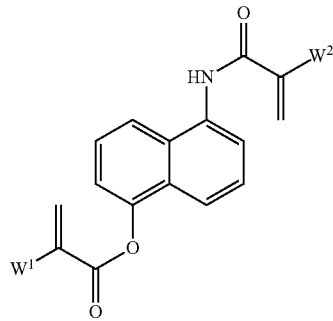
(5-1)

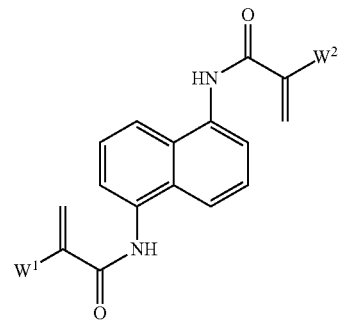
(5-6)

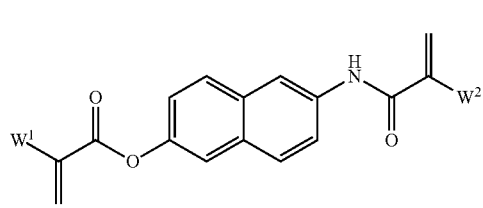
(5-2)

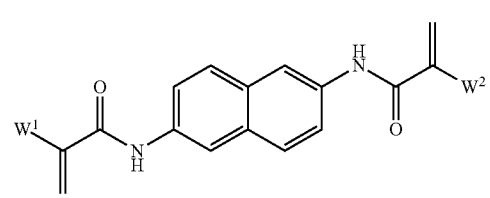
(5-7)

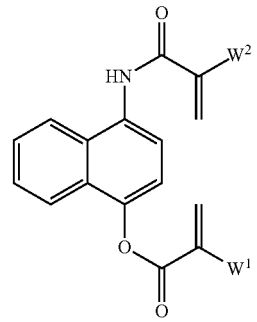
(5-3)

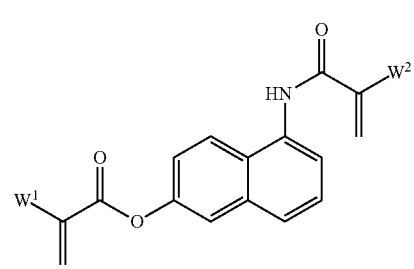
(5-4)

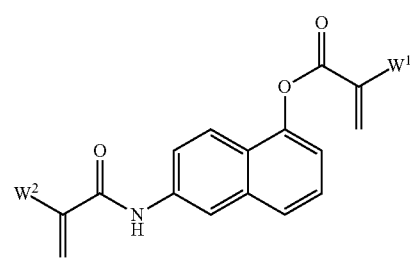
(5-5)

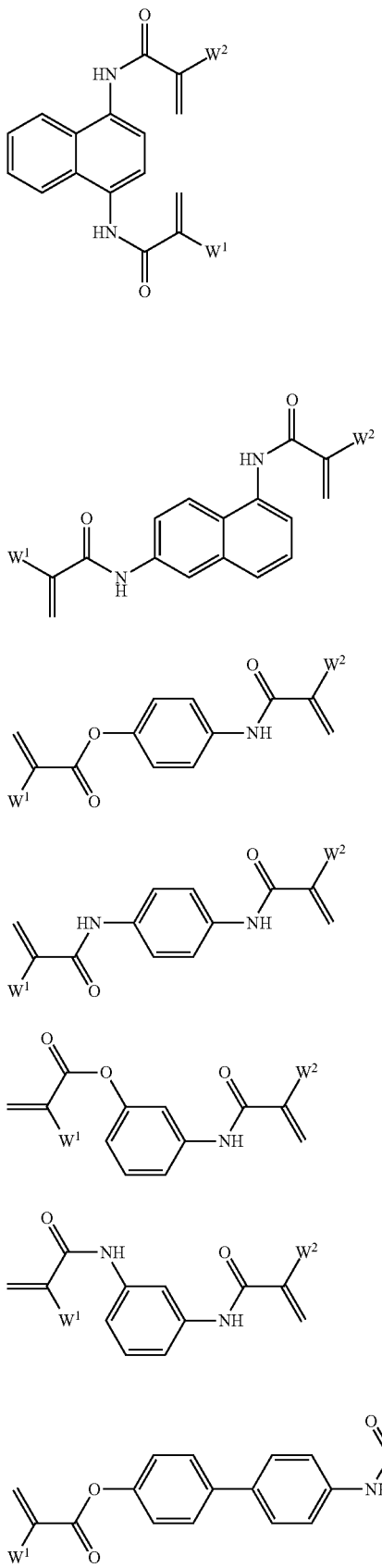

In the formula, $W^1$ and $W^2$ may be the same or different, and denote —H or —$CH_3$ group.

The above-mentioned liquid crystal composition may contain a monomer having a structure for producing a radical by hydrogen abstraction reaction by light irradiation or a structure for producing a radical by self-cleavage reaction by light irradiation.

In the case where a compound represented by one of the above-mentioned formulas (1), (2), and (5-1) to (5-18) is used alone as a radical polymerizable monomer, a polymer layer (PSA layer) can be formed but it is needed to irradiate with light containing a wavelength component around 300 nm for a long time. However, the structure in a panel of a liquid crystal display device may possibly be deteriorated by long time irradiation of the wavelength component around 300 nm and the capability as a display device is impaired in some cases.

Accordingly, in terms of quality retention, it is efficient to shorten the light irradiation time needed for polymerization reaction by using the above-mentioned monomer having a structure for producing a radical by light irradiation in combination. Further, the above-mentioned monomer having a structure for producing a radical by light irradiation is preferable to have a structure for efficiently generating a radical by irradiating with light having wavelength component of 300 nm or longer and more preferably 350 nm or longer.

Examples of the above-mentioned monomer having a structure for producing a radical by hydrogen abstraction reaction by light irradiation may include compounds represented by the following chemical formula (3).

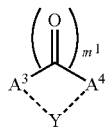
(3)

In the formula, $A^3$ denotes an aromatic ring;

$A^4$ denotes an aromatic ring same as or different from $A^3$, or a straight or branched alkyl or alkenyl group with 1 to 12 carbon atoms;

at least one of $A^3$ and $A^4$ contains a -$Sp^3$-P group;

an aromatic ring included in at least one of $A^3$ and $A^4$ is a benzene ring or a biphenyl ring;

a hydrogen atom included in $A^3$ and $A^4$ may be substituted with a -$Sp^3$-P group, a halogen atom, —CN, —NO$_2$, —NCO, —NCS, —OCN, —SCN, —SF$_5$, or an alkyl, alkenyl or aralkyl group with 1 to 12 carbon atoms, and the alkyl and alkenyl groups may be straight or branched;

two neighboring hydrogen atoms included in $A^3$ and $A^4$ may be substituted with a straight or branched alkylene or alkenylene group with 1 to 12 carbon atoms to form a ring structure;

a hydrogen atom included in the alkyl, alkenyl, alkylene, alkenylene or aralkyl group of $A^3$ and $A^4$ may be substituted with a -$Sp^3$-P group;

a —CH$_2$— group included in the alkyl, alkenyl, alkylene, alkenylene or aralkyl group of $A^3$ and $A^4$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, or —OCO—CH═CH— group unless an oxygen atom, a sulfur atom, and a nitrogen atom neighbor with one another;

P denotes a radical polymerizable group;

$Sp^3$ denotes a straight, branched, or cyclic alkylene or alkyleneoxy group with 1 to 6 carbon atoms, or a direct bond;

$m^1$ denotes 1 or 2;

a dotted line part connecting $A^3$ and Y and a dotted line part connecting $A^4$ and Y represent that bond through Y may exist between $A^3$ and $A^4$; and Y denotes —CH$_2$—, —CH$_2$CH$_2$—, —CH═CH—, —O—, —S—, —NH—, —N(CH$_3$)—, —N(C$_2$H$_5$)—, —N(C$_3$H$_7$)—, —N(C$_4$H$_9$)—, —OCH$_2$—, —CH$_2$O—, —SCH$_2$—. —CH$_2$S— groups, or a direct bond.

Examples of a compound represented by the above-mentioned formula (3) may include compounds represented by one of the following formulas (6-1) to (6-8).

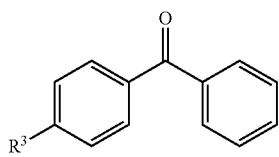
(6-1)

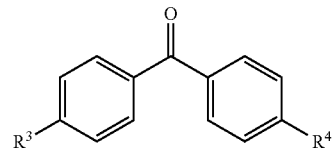
(6-2)

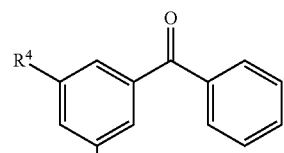
(6-3)

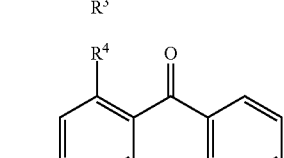
(6-4)

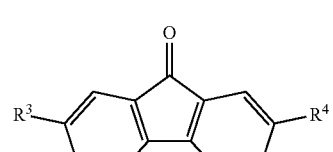
(6-5)

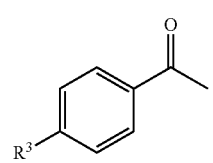
(6-6)

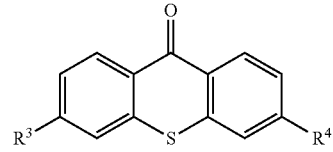
(6-7)

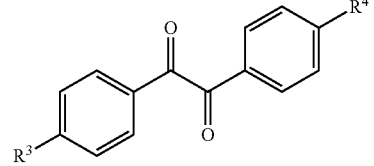
(6-8)

In the formula, $R^3$ and $R^4$ may be the same or different, and denote a -$Sp^8$-P group, a hydrogen atom, a halogen atom, —CN, —NO$_2$, —NCO, —NCS, —OCN, —SCN, —SF$_5$, or a straight or branched alkyl or aralkyl with 1 to 12 carbon atoms, or phenyl group;

at least one of $R^3$ and $R^4$ contains a -$Sp^8$-P group;

P denotes a radical polymerizable group;

$Sp^8$ denotes a straight, branched or cyclic alkylene or alkyleneoxy group with 1 to 6 carbon atoms, or a direct bond;

in the case where at least one of $R^3$ and $R^4$ is an alkyl or aralkyl with 1 to 12 carbon atoms or phenyl group, a hydrogen atom included in $R^3$ and $R^4$ may be substituted with a fluorine atom, a chlorine atom, or a -$Sp^8$-P group; and a —CH$_2$— group included in $R^3$ and $R^4$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, or —OCO—CH═CH— group unless an oxygen atom, a sulfur atom, and a nitrogen atom neighbor one another.

A compound having a structure represented by one of the above-mentioned formulas (6-1) to (6-6) has an absorption wavelength region up to around 380 nm and a compound represented by the above-mentioned formula (6-7) or (6-8) has an absorption wavelength region up to around 430 nm. Accordingly, use of a compound having a structure represented by one of the formulas (6-1) to (6-8) in combination can increase the polymerization reaction speed by light irradiation and improve the throughput in production of a liquid crystal display device even if light with short wavelength (e.g. light with wavelength shorter than 300 nm) is cut. Further, since having a wider light absorption wavelength region than a compound having a structure represented by one of the above-mentioned formulas (6-1) to (6-6) to increase the light utilization efficiency, a compound represented by the formula (6-7) or (6-8) is capable of polymerizing a radical polymerizable monomer by light irradiation even after a polarizing plate is respectively stuck to a pair of substrates of a liquid crystal display device.

Example of the above-mentioned monomer having a structure for producing a radical by self-cleavage reaction by light irradiation may include compounds represented by the following chemical formula (4).

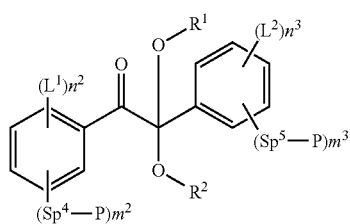

(4)

In the formula,
R$^1$ denotes a straight or branched alkyl or alkenyl group with 1 to 4 carbon atoms, or -Sp$^6$-P;
R$^2$ denotes a straight or branched alkyl or alkenyl group with 1 to 4 carbon atoms, or -Sp$^7$-P;
P denotes the same or different radical polymerizable group and the total number is 2 or more;
Sp$^4$ denotes a straight, branched, or cyclic alkylene, alkyleneoxy, or alkylenecarbonyloxy group with 1 to 6 carbon atoms, or a direct bond; and in the case where m$^2$ is 2 or more, Sp$^4$ may be the same or different;
Sp$^5$ denotes a straight, branched, or cyclic alkylene, alkyleneoxy, or alkylenecarbonyloxy group with 1 to 6 carbon atoms, or a direct bond and in the case where m$^3$ is 2 or more, Sp$^5$ may be the same or different;
Sp$^6$ denotes a straight, branched, or cyclic alkylene, alkyleneoxy, or alkylenecarbonyloxy group with 1 to 6 carbon atoms;
Sp$^7$ denotes a straight, branched, or cyclic alkylene, alkyleneoxy, or alkylenecarbonyloxy group with 1 to 6 carbon atoms;
L$^1$ denotes —F, —OH, or a straight or branched alkyl, straight or branched alkenyl, or aralkyl group with 1 to 12 carbon atoms; and in the case where n$^2$ is 2 or more, L$^1$ may be the same or different;

in the case where two L$^1$s are bonded to two neighboring carbon atoms in an aromatic ring, a ring structure may be formed by bonding each other, and two L$^1$s may be the same or different and be a straight or branched alkylene or alkenylene group with 1 to 12 carbon atoms;
L$^2$ denotes —F, —OH, or a straight or branched alkyl, straight or branched alkenyl, or aralkyl group with 1 to 12 carbon atoms; and in the case where n$^3$ is 2 or more, L$^2$ may be the same or different;
in the case where two L$^2$s are bonded to two neighboring carbon atoms in an aromatic ring, a ring structure may be formed by bonding each other, and two L$^2$s may be the same or different and be a straight or branched alkylene or alkenylene group with 1 to 12 carbon atoms;
one or more hydrogen atoms included in the alkyl, alkenyl, alkylene, alkenylene or aralkyl group of L$^1$ and L$^2$ may be substituted with —F or —OH group;
a —CH$_2$— group included in the alkyl, alkenyl, alkylene, alkenylene or aralkyl group of L$^1$ and L$^2$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, —OCO—CH═CH—, -Sp$^4$-P, or -Sp$^5$-P group unless an oxygen atom, a sulfur atom, and a nitrogen atom neighbor one another;
m$^2$ denotes an integer of 1 to 3;
m$^3$ denotes an integer of 0 to 3;
n$^2$ denotes an integer of 0 to 4;
n$^3$ denotes an integer of 0 to 4;
the total of m$^2$ and n$^2$ is an integer of 1 to 5;
the total of m$^3$ and n$^3$ is an integer of 0 to 5; and
the total of m$^2$ and m$^3$ is an integer of 1 to 6.)

Examples of a compound represented by the above-mentioned formula (4) may include compounds represented by the following formula (7).

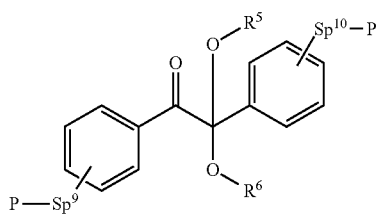

(7)

In the formula,
R$^5$ denotes a straight or branched alkyl or alkenyl group with 1 to 4 carbon atoms;
R$^6$ denotes a straight or branched alkyl or alkenyl group with 1 to 4 carbon atoms;
P denotes the same or different radical polymerizable group;
Sp$^9$ denotes a straight, branched, or cyclic alkylene, alkyleneoxy, or alkylenecarbonyloxy group with 1 to 6 carbon atoms, or a direct bond; and
Sp$^{10}$ denotes a straight, branched, or cyclic alkylene, alkyleneoxy, or alkylenecarbonyloxy group with 1 to 6 carbon atoms, or a direct bond.

Examples of P contained in compounds represented by the above-mentioned formulas (1), (3), (4), (6-1) to (6-8), and (7) may include (meth)acryloyloxy, (meth)acryloylamino, vinyl, and vinyloxy group.

Another aspect of the present invention is a liquid crystal display device which has a pair of substrates, a liquid crystal layer containing a liquid crystal material sandwiched between the pair of the substrates, and a polymer layer formed on at least one of the substrates and configured to control alignment of liquid crystal molecules, and in which the polymer layer is formed by polymerizing one or more kinds monomers and at least one of the monomers is a compound represented by the following chemical formula (1). The polymer layer may be formed by polymerizing one or more kinds monomers added to the liquid crystal layer.

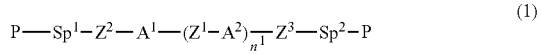

In the formula,
P denotes the same or different radical polymerizable group;
$Sp^1$ and $Sp^2$ may be the same or different, and respectively denote a straight or branched alkylene or alkyleneoxy group with 1 to 6 carbon atoms, or a direct bond;
$A^1$ denotes a divalent alicyclic, aromatic monocyclic, or condensed polycyclic hydrocarbon group;
$A^2$ denotes a phenylene group;
a —$CH_2$— group included in $A^1$ and $A^2$ may be substituted with an —O— or a —S— group unless neighboring each other;
a —CH= group included in $A^1$ and $A^2$ may be substituted with a —N= group unless neighboring each other;
a hydrogen atom included in $A^1$ and $A^2$ may be substituted with a fluorine atom, a chlorine atom, a —CN group, or a straight or branched alkyl, alkoxy, alkylcarbonyl, alkoxycarbonyl or alkylcarbonyloxy group with 1 to 12 carbon atoms and further one or more of carbon atoms in these groups may be substituted with a silicon atom;
$Z^1$, $Z^2$, and $Z^3$ may be the same or different, and denote —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —NRCO—, —CONR—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH=CH—, —CF=CF—, —C≡C—, —CH=CH—COO—, —OCO—CH=CH— groups, or a direct bond;
at least one of $Z^1$, $Z^2$, and $Z^3$ denotes —NRCO— or —CONR— group;
R denotes a hydrogen atom, or a straight alkyl or alkenyl group with 1 to 6 carbon atoms; and
$n^1$ denotes 0 or 1.
As long as being formed by indispensably using these constituent elements, the configuration of the liquid crystal display device of this aspect is not particularly limited by other constituent elements.
Practical examples of the respective constituent elements of the liquid crystal display device of this aspect may include the following embodiments (a) to (i) which are the same as those exemplified for the monomers and liquid crystal compositions according to an aspect of the present invention. That is,
(a) an embodiment in which $A^1$ included in a compound represented by the above-mentioned formula (1) is benzene-1,2-diyl, benzene-1,3-diyl, benzene-1,4-diyl, pyridine-2,3-diyl, pyridine-2,4-tolyl, pyridine-2,5-diyl, pyridine-2,6-diyl, naphthalene-1,2-diyl, naphthalene-1,4-diyl, naphthalene-1,5-diyl, naphthalene-1,8-diyl, naphthalene-2,3-diyl, naphthalene-2,6-diyl, naphthalene-2,7-diyl, cyclohexane-1,2-diyl, cyclohexane-1,3-diyl, cyclohexane-1,4-diyl, decahydronaphthalene-1,2-diyl, decahydronaphthalene-1,4-diyl, decahydronaphthalene-1,5-diyl, decahydronaphthalene-1,8-diyl, decahydronaphthalene-2,3-diyl, decahydronaphthalene-2,6-diyl, indane-1,1-diyl, indane-1,3-diyl, indane-1,5-diyl, indane-1,6-diyl, phenanthrene-1,6-diyl, phenanthrene-1,8-diyl, phenanthrene-1,9-diyl, phenanthrene-2,7-diyl, phenanthrene-2,9-diyl, phenanthrene-3,6-diyl, phenanthrene-3,9-diyl, phenanthrene-9,10-diyl, anthracene-1,4-diyl, anthracene-1,5-diyl, anthracene-1,9-diyl, anthracene-2,3-diyl, anthracene-2,6-diyl, anthracene-2,9-diyl, or anthracene-9,10-diyl group and $A^2$ is benzene-1,2-diyl, benzene-1,3-diyl, or benzene-1,4-diyl group;
(b) an embodiment in which a compound represented by the above-mentioned formula (1) is a compound represented by the above-mentioned formula (2);
(c) an embodiment in which a compound represented by the above-mentioned formula (1) is a compound represented by one of the above-mentioned formulas (5-1) to (5-18);
(d) an embodiment in which the monomer further include a monomer having a structure for producing a radical by hydrogen abstraction reaction by light irradiation or a structure for producing a radical by self-cleavage reaction by light irradiation;
(e) an embodiment in which the above-mentioned monomer having a structure for producing a radical by hydrogen abstraction reaction by light irradiation is a compound represented by the above-mentioned formula (3);
(f) an embodiment in which the compound represented by the above-mentioned formula (3) is a compound represented by one of the above-mentioned formulas (6-1) to (6-8);
(g) an embodiment in which the above-mentioned monomer having a structure for producing a radical by self-cleavage reaction by light irradiation is a compound represented by the above-mentioned formula (4);
(h) an embodiment in which a compound represented by the above-mentioned formula (4) is a compound represented by the above-mentioned formula (7); and
(i) an embodiment in which P contained in compounds represented by the above-mentioned formulas (1), (3), (4), (6-1) to (6-8), and (7) is (meth)acryloyloxy, (meth)acryloylamino, vinyl, or vinyloxy group.
Another aspect of the present invention is a production method for a liquid crystal display device involving: steps of injecting a liquid crystal composition containing a liquid crystal material, and one or more kind monomers between a pair of substrates; and forming a polymer layer for controlling alignment of liquid crystal molecules on substrates by irradiating the liquid crystal composition with light and thereby polymerizing the monomers wherein at least one monomer is a compound represented by the following chemical formula (1).

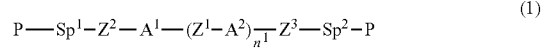

In the formula,
P denotes the same or different radical polymerizable group;
$Sp^1$ and $Sp^2$ may be the same or different, and respectively denote a straight or branched alkylene or alkyleneoxy group with 1 to 6 carbon atoms, or a direct bond;
$A^1$ denotes a divalent alicyclic, aromatic monocyclic, or condensed polycyclic hydrocarbon group;

$A^2$ denotes a phenylene group;

a —$CH_2$— group included in $A^1$ and $A^2$ may be substituted with an —O— or a —S— group unless neighboring each other;

a —CH= group included in $A^1$ and $A^2$ may be substituted with a —N= group unless neighboring each other;

a hydrogen atom included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms, and further one or more of carbon atoms in these groups may be substituted with a silicon atom;

$Z^1$, $Z^2$, and $Z^3$ may be the same or different, and denote —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —NRCO—, —CONR—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH=CH—, —CF=CF—, —C≡C—, —CH=CH—COO—, —OCO—CH=CH— groups, or a direct bond;

at least one of $Z^1$, $Z^2$, and $Z^3$ denotes —NRCO— or —CONR— group;

R denotes a hydrogen atom, or a straight alkyl or alkenyl group with 1 to 6 carbon atoms; and $n^1$ denotes 0 or 1.

A production method for a liquid crystal display device according to an aspect of the present invention involves a step of injecting a liquid crystal composition containing a liquid crystal material, and one or more kind monomers between a pair of substrates. Herein, the liquid crystal material and monomers to be used may be the same as described in the above-mentioned liquid crystal display device in an aspect of the present invention.

The above-mentioned step for forming the polymer layer may be a step carried out in a state that voltage not lower than the threshold value is applied to the liquid crystal layer. At the time of carrying out the PSA polymerization step, a polymer is formed following the liquid crystal molecules aligned in the state that voltage not lower than the threshold value is applied to the liquid crystal layer by irradiating with light in the state that voltage not lower than the threshold value is applied. Therefore, the polymer layer to be formed is to have a structure for defining the pre-tilt angle to the liquid crystal molecules even in the state that no voltage is applied thereafter.

The above-mentioned step for forming the polymer layer may be a step carried out in a state that voltage not lower than the threshold value is not applied to the liquid crystal layer. Even in the state that voltage not lower than the threshold value is not applied, a polymer layer for reinforcing the initial alignment of liquid crystal molecules can be formed.

As long as being formed by indispensably involving the above-mentioned step as a constituent of the production method for a liquid crystal display device in this aspect, the production method is not particularly limited by other steps.

Practical examples of the production method for a liquid crystal display device in this aspect include the following embodiments (j) to (r) which are the same as the contents exemplified for the monomers and liquid crystal compositions according to an aspect of the present invention. That is, (j) an embodiment in which $A^1$ included in a compound represented by the above-mentioned formula (1) is benzene-1,2-diyl, benzene-1,3-diyl, benzene-1,4-diyl, pyridine-2,3-diyl, pyridine-2,4-tolyl, pyridine-2,5-diyl, pyridine-2,6-diyl, naphthalene-1,2-diyl, naphthalene-1,4-diyl, naphthalene-1,5-diyl, naphthalene-1,8-diyl, naphthalene-2,3-diyl, naphthalene-2,6-diyl, naphthalene-2,7-diyl, cyclohexane-1,2-diyl, cyclohexane-1,3-diyl, cyclohexane-1,4-diyl, decahydronaphthalene-1,2-diyl, decahydronaphthalene-1,4-diyl, decahydronaphthalene-1,5-diyl, decahydronaphthalene-1,8-diyl, decahydronaphthalene-2,3-diyl, decahydronaphthalene-2,6-diyl, indane-1,1-diyl, indane-1,3-diyl, indane-1,5-diyl, indane-1,6-diyl, phenanthrene-1,6-diyl, phenanthrene-1,8-diyl, phenanthrene-1,9-diyl, phenanthrene-2,7-diyl, phenanthrene-2,9-diyl, phenanthrene-3,6-diyl, phenanthrene-3,9-diyl, phenanthrene-9,10-diyl, anthracene-1,4-diyl, anthracene-1,5-diyl, anthracene-1,9-diyl, anthracene-2,3-diyl, anthracene-2,6-diyl, anthracene-2,9-diyl, or anthracene-9,10-diyl group, and $A^2$ is benzene-1,2-diyl, benzene-1,3-diyl, or benzene-1,4-diyl group;

(k) an embodiment in which a compound represented by the above-mentioned formula (1) is a compound represented by the above-mentioned formula (2);

(l) an embodiment in which a compound represented by the above-mentioned formula (1) is a compound represented by one of the above-mentioned formulas (5-1) to (5-18);

(m) an embodiment in which the above-mentioned liquid crystal composition further contain a monomer having a structure for producing a radical by hydrogen abstraction reaction by light irradiation or a structure for producing a radical by self-cleavage reaction by light irradiation.

(n) an embodiment in which the above-mentioned monomer having a structure for forming a radical by hydrogen abstraction reaction by light irradiation is a compound represented by the above-mentioned formula (3);

(o) an embodiment in which the compound represented by the above-mentioned formula (3) is a compound represented by one of the above-mentioned formulas (6-1) to (6-8);

(p) an embodiment in which the above-mentioned monomer having a structure for producing a radical by self-cleavage reaction by light irradiation is a compound represented by the above-mentioned formula (4);

(q) an embodiment in which a compound represented by the above-mentioned formula (4) is a compound represented by the above-mentioned formula (7); and (r) an embodiment in which P contained in compounds represented by the above-mentioned formulas (1), (3), (4), (6-1) to (6-8), and (7) is (meth)acryloyloxy, (meth)acryloylamino, vinyl, or vinyloxy group.

Advantageous Effects of Invention

According to an aspect of the present invention, it is made possible to provide a monomer and a liquid crystal composition capable of forming a polymer layer for maintaining high display quality even in high temperature and high humidity environments, a liquid crystal display device capable of maintaining high display quality even in high temperature and high humidity environments, and a production method for a liquid crystal display device capable of maintaining high display quality even in high temperature and high humidity environments.

DESCRIPTION OF EMBODIMENTS

Figure 1:
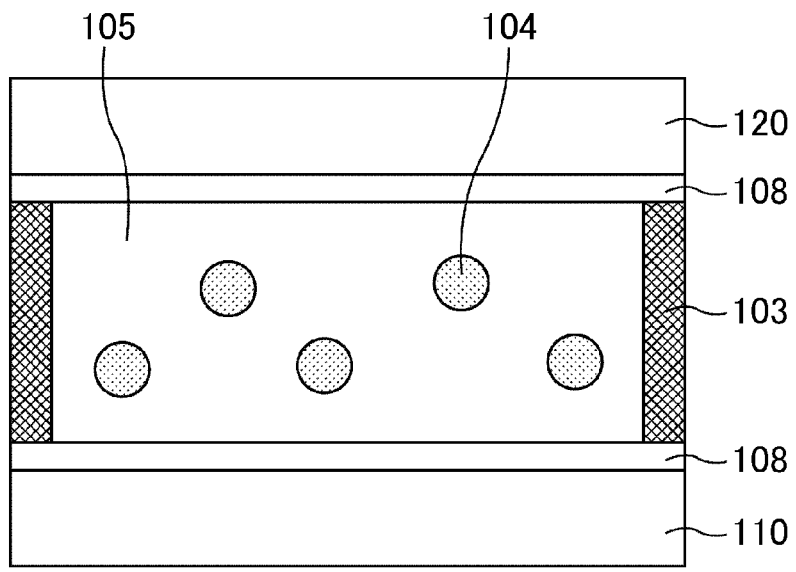
FIG. 1 is a schematic view of a cross section of a liquid crystal display device of Embodiment 1 before a PSA polymerization step.

An aspect of the present invention will be described in more detail referring to the drawings in the following embodiments, but is not limited to these embodiments.

A liquid crystal display device produced using a liquid crystal composition in an aspect of the present invention, a liquid crystal display device in an aspect of the present invention, and a liquid crystal display device produced by the production method in an aspect of the present invention exhibit excellent display properties while being used for display devices, for example, a television, a personal computer, a mobile phone, an information display, etc.

Embodiment 1

Figure 2:
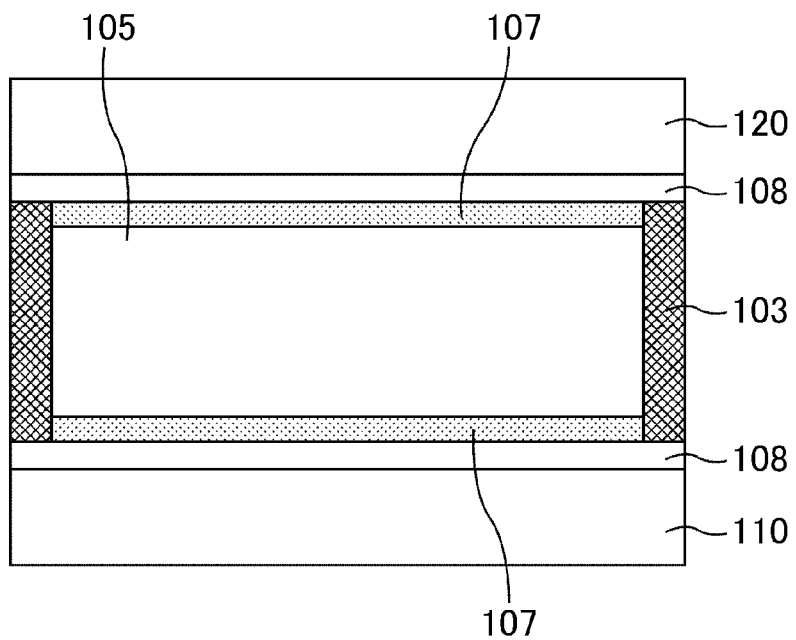
FIG. 2 is a schematic view of a cross section of a liquid crystal display device of Embodiment 1 after the PSA polymerization step.

Hereinafter, one example of a liquid crystal display device of Embodiment 1 will be described. FIG. 1 and FIG. 2 are schematic cross sectional views of a liquid crystal display device of Embodiment 1 and FIG. 1 illustrates the view before a PSA polymerization step and FIG. 2 illustrates the view after the PSA polymerization step. As illustrated in FIG. 1 and FIG. 2, the liquid crystal display device of Embodiment 1 has an array substrate 110, a color filter substrate 120, and a liquid crystal layer 105 sandwiched between a pair of the substrates, that is, the array substrate 110 and the color filter substrate 120. The array substrate 110 has an insulating transparent substrate made of a material such as glass or the like, various kinds of wiring formed on the transparent substrate, a pixel electrode, and a TFT (thin film transistor). The color filter substrate 120 has an insulating transparent substrate made of a material such as glass or the like, a color filter formed on the transparent substrate, a black matrix, and a common electrode. The array substrate 110 and the color filter substrate 120 are respectively provided with an alignment film 108 on the surfaces in the liquid crystal layer 105 side.

As illustrated in FIG. 1, before the PSA polymerization step, the liquid crystal layer 105 contains a liquid crystal material and a radical polymerizable monomer 104. The radical polymerizable monomer 104 is a compound represented by the above-mentioned formula (1) and more practically a compound represented by the above-mentioned formula (2) and furthermore practically a compound represented by one of the above-mentioned formulas (5-1) to (5-18).

The radical polymerizable monomer 104 produces a radical by irradiating the liquid crystal layer 105 with light and using the radical as active species, the radical polymerizable group of the radical polymerizable monomer 104 successively starts and promotes chain polymerization to be polymerized. The polymer formed by the polymerization is deposited in form of a polymer layer (PSA layer) 107 on the alignment film 108 formed on the substrates 110 and 120 as illustrated in FIG. 2.

As described above, it is supposed that stains and display unevenness generated in high temperature and high humidity environments are caused by penetration of the liquid crystal layer with water, an impurity, or the like. If the liquid crystal layer is penetrated with water, an impurity, or the like, the voltage holding ratio (VHR) is lowered and direct current offset voltage (hereinafter, also referred to as remaining DC voltage) tends to be generated easily in the inside of the liquid crystal layer. Since having an amide group, the radical polymerizable monomer 104 can form a hydrogen bond with water, a water-soluble impurity, or the like. Because of that, the remaining amount of water, an impurity, or the like in the liquid crystal layer can be lessened by forming the polymer layer 107 by using the radical polymerizable monomer 104 and thus decrease of the voltage holding ratio (VHR) and generation of the remaining DC voltage can be suppressed. As a result, it is made possible to obtain a liquid crystal display device which can keep high display quality even in high temperature and high humidity environments.

In a conventional PSA technique, a polymerization initiator is usually used but in the case where a polymerization initiator (e.g. Irgacure 651 or the like) is used, products formed by cleavage resulted from ultraviolet irradiation float as impurities in a liquid crystal and consequently lower the voltage holding ratio (VHR). In Embodiment 1, since the radical polymerizable monomer 104 produce a radical by itself, such a polymerization initiator is not required and thus impurities derived from the polymerization initiator are not produced. As a result, high voltage holding ratio (VHR) can be maintained. Further, since having two polymerizable groups, the radical polymerizable monomer 104 is easy to be taken in a polymer layer 107 when the polymer layer 107 is formed and hardly remains as an impurity in the liquid crystal layer and consequently does not lower the voltage holding ratio (VHR).

As illustrated in FIG. 2, in Embodiment 1, the polymer layer 107 is formed on the surface of the alignment film 108 formed on the array substrate 110 and the color filter substrate 120. Between the array substrate 110 and the color filter substrate 120, a sealing material 103 is stuck to the alignment film 108 along the outer rim of these substrates 110 and 120 and the liquid crystal layer 105 is enclosed between the array substrate 110 and the color filter substrate 120 by the sealing material 103. Irradiation of the liquid crystal layer 105 with light is carried out after sealing the liquid crystal layer 105 by the sealing material 103 so that the polymer layer 107 is formed in the region surrounded with the sealing material 103.

In Embodiment 1, at the time of carrying out the PSA polymerization step, a polymer is formed following the liquid crystal molecules aligned in the state that voltage not lower than the threshold value is applied to the liquid crystal layer 105 by irradiating the liquid crystal layer 105 with light in the state that voltage not lower than the threshold value is applied. In this case, the polymer layer to be formed is to have a structure for defining the pre-tilt angle to the liquid crystal molecules even in the state that no voltage is applied thereafter. Further, in the case where one or more kind radical polymerizable monomers in Embodiment 1 are used, a polymer layer can be produced and liquid crystal molecules can be aligned in a specified direction on the substrate face without applying voltage not lower than the threshold value to the liquid crystal layer 105 at the time of the PSA polymerization step by carrying out an alignment treatment for the alignment film 108.

Other constituent elements of a liquid crystal display device of Embodiment 1 will be described in detail.

In the liquid crystal display device of Embodiment 1, the array substrate 110, the liquid crystal layer 105 and the color filter substrate 120 are layered in this order from the back side of the liquid crystal display device to the observation side. Polarizing plates are installed in the back side of the array substrate 110 and in the observation side of the color filter substrate 120. A retardation film may be arranged for these polarizing plates and the polarizing plates may be circular polarization plates.

The liquid crystal display device of Embodiment 1 may be a transmission type, a reflection type, and a transmission/reflection combined type. In the case of a transmission type or a transmission/reflection combined type, the liquid crystal display device of Embodiment 1 is further equipped with a back light unit. The back light unit is arranged further in the back side of the array substrate 110 and arranged in a manner that light is transmitted through the array substrate 110, the liquid crystal layer 105, and the color filter substrate 120 in this order. In the case of a reflection type or a transmission/reflection combined type, the array substrate 110 is equipped with a reflector for reflecting light from outside. Further, in a region in which at least the reflected light is used for display, the polarizing plate of the color filter substrate 120 is required to have a circular polarization plate equipped with so-called λ/4 retardation film.

The liquid crystal layer 105 is filled with a liquid crystal material having a property of aligning in a specified direction by applying a certain voltage. The alignment property of the liquid crystal molecules in the liquid crystal layer 105 is controlled based on application of voltage not lower than the threshold value. The liquid crystal material may be one having positive anisotropy of dielectric constant and one having negative anisotropy of dielectric constant.

The above-mentioned alignment film 108 may be either a vertical alignment film or a horizontal alignment film. A vertical alignment film means an alignment film by which liquid crystal molecules are aligned vertically to the substrate face at the time of no voltage application and may be subjected to an alignment treatment. Vertical alignment means that an average initial tilt angle of liquid crystal molecules to the substrate face is 60° to 90° and preferably 80° to 90°. A horizontal alignment film means an alignment film by which liquid crystal molecules are aligned horizontally to the substrate face at the time of no voltage application and may be subjected to an alignment treatment. Horizontal alignment means that an average initial tilt angle of liquid crystal molecules to the substrate face is 0° to 30° and preferably 0° to 10°. "Tilt angle" is an angle between the major axis of liquid crystal molecules and the substrate face and is defined in a range of 0° to 90° and "average tilt angle" is sometimes referred to as "tilt angle". The average tilt angle of liquid crystal molecules to each substrate at the time of no voltage application is called as "average initial tilt angle" and hereinafter, simply referred to also as "pre-tilt angle". An alignment treatment method may be a rubbing method, a photo-alignment method, etc.

The array substrate 110 and the color filter substrate 120 may be stuck by using a sealing material and those which are hardened by heat, those which are hardened by ultraviolet irradiation, and those which are hardened by both heat and ultraviolet irradiation may be used as the sealing material.

Regarding the liquid crystal display device of Embodiment 1, the liquid crystal display device (e.g. a mobile phone, a monitor, a liquid crystal TV (television), and information display) is disassembled and the monomer components existing in the polymer layer are analyzed by carrying out chemical analysis using NMR (nuclear magnetic resonance), FT-IR (Fourier transform infrared spectroscopy), MS (mass spectrometry), etc. and thus the types of the monomer components can be determined.

Embodiment 2

Embodiment 2 is the same as Embodiment 1, except that another monomer having a structure for producing a radical by light irradiation is used in addition to the radical polymerizable monomer used in Embodiment 1.

Figure 3:
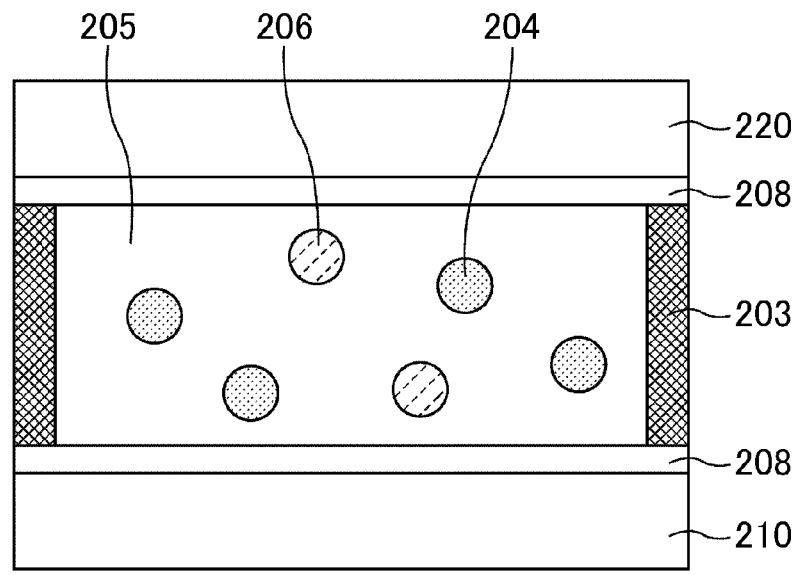
FIG. 3 is a schematic view of a cross section of a liquid crystal display device of Embodiment 2 before a PSA polymerization step.
Figure 4:
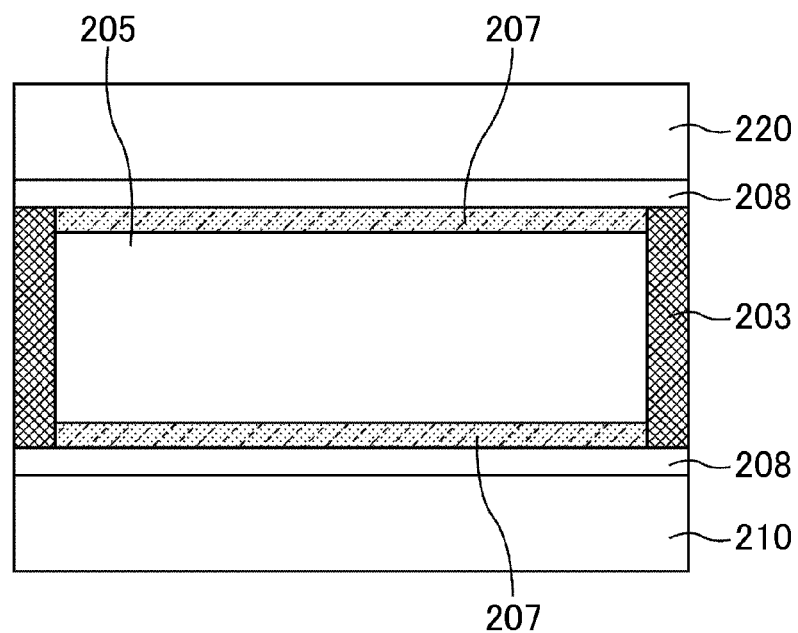
FIG. 4 is a schematic view of a cross section of a liquid crystal display device of Embodiment 2 after a PSA polymerization step.

Hereinafter, one example of a liquid crystal display device of Embodiment 2 will be described. FIG. 3 and FIG. 4 are schematic views of a cross section of a liquid crystal display device of Embodiment 2. FIG. 3 illustrates a view before the PSA polymerization step and FIG. 4 illustrates a view after the PSA polymerization step. As illustrated in FIG. 3 and FIG. 4, the liquid crystal display device of Embodiment 2 has an array substrate 210, a color filter substrate 220, and a liquid crystal layer 205 sandwiched between a pair of the substrates, that is, the array substrate 210 and the color filter substrate 220. The array substrate 210 has an insulating transparent substrate made of a material such as glass or the like, various kinds of wiring formed on the transparent substrate, a pixel electrode, a TFT, etc. The color filter substrate 220 has an insulating transparent substrate made of a material such as glass or the like, a color filter formed on the transparent substrate, a black matrix, and a common electrode. The array substrate 210 and the color filter substrate 220 are respectively provided with an alignment film 208 on the surfaces in the liquid crystal layer 205 side.

As illustrated in FIG. 3, before the PSA polymerization step, the liquid crystal layer 205 contains a liquid crystal material, a first radical polymerizable monomer 204, and a second radical polymerizable monomer 206. The first radical polymerizable monomer 204 is a compound represented by the above-mentioned formula (1) and more practically a compound represented by the above-mentioned formula (2) and furthermore practically a compound represented by one of the above-mentioned formula (5-1) to (5-18). The second radical polymerizable monomer 206 is a monomer having a structure for producing a radical by light irradiation and may be a compound represented by the above-mentioned formula (3) or (6-1) to (6-8) and having a structure for producing a radical by hydrogen abstraction reaction by light irradiation and a compound represented by the above-mentioned formula (4) or (7) and having a structure for producing a radical by self-cleavage reaction by light irradiation. Use of a monomer having a structure for producing a radical by light irradiation in combination can promote polymerization reaction with no need of newly adding a polymerization initiator and prevent decrease of voltage holding ratio (VHR).

Both of the first radical polymerizable monomer 204 and the second radical polymerizable monomer 206 independently produce a radical by irradiating the liquid crystal layer 205 with light and using the radical as active species, the radical polymerizable groups of the first radical polymerizable monomer 204 and the second radical polymerizable monomer 206 successively start and promote chain polymerization to be polymerized. The polymer formed by the polymerization is deposited in the form of a polymer layer (PSA layer) 207 on the alignment film 208 formed on the substrates 210 and 220 as illustrated in FIG. 4.

As illustrated in FIG. 4, in Embodiment 2, the polymer layer 207 is formed on the surface of the alignment film 208 formed on the array substrate 210 and the color filter substrate 220. Between the array substrate 210 and the color filter substrate 220, a sealing material 203 is stuck to the alignment film 208 along the outer rim of these substrates 210 and 220 and the liquid crystal layer 205 is enclosed between the array substrate 210 and the color filter substrate 220 by the sealing material 203. Irradiation of the liquid crystal layer 205 with light is carried out after sealing the liquid crystal layer 205 by the sealing material 203 so that the polymer layer 207 is formed in the region surrounded with the sealing material 203.

In the same manner as in Embodiment 1, in Embodiment 2, it is also made possible to obtain a liquid crystal display device which can keep high display quality even in high temperature and high humidity environments. Use of a monomer having a structure for producing a radical by light irradiation in combination makes it possible to form the polymer layer within a short irradiation time and thus improve the throughput.

Synthesis Example

Hereinafter, described is a synthesis example for synthesizing 1-methacrylamino-5-methacryloxynaphthalene as a practical example of a radical polymerizable monomer represented by the above-mentioned formula (1).

As illustrated in the following chemical reaction formula (8), 2.0 g of 1-amino-5-hydroxynaphthalene made available in markets was dissolved in 14 g of tetrahydrofuran (THF) and 3.18 g of triethylamine (TEA) and 0.15 g of 4-dimethylaminopyridine (DMAP) were added to the obtained solution and stirred and cooled until the solution temperature became 15° C. A solution obtained by dissolving 4.84 g of methacrylic anhydride in 5 ml of THF was dropwise added to the above-mentioned resulting solution in 10 minutes. On completion of the dropwise addition, the solution mixture was stirred for 2 hours and mixed with 30 g of an aqueous 1% HCl solution and stirred further for 10 minutes. Thereafter, extraction was carried out with 55 g of methyl isobutyl ketone and the extract was washed with pure water 4 times. Thereafter, the residue obtained by removing the solvent was refined by column chromatography using an ethyl acetate/hexane (10/90) solution as an eluent to obtain the following compound at 22% yield.

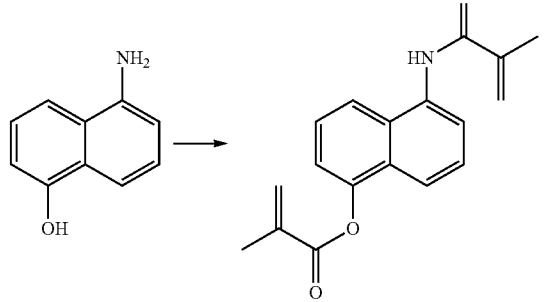

(8)

The analysis result of the obtained compound by $^1$H-NMR (400 MHz) is as follows. $^1$H-NMR (CDCl$_3$, ppm):

δ=2.16 (s, 3H, methyl group), 2.17 (s, 3H, methyl group), 5.57 (s, 1H, vinyl group), 5.88 (s, 1H, vinyl group), 5.96 (s, 1H, vinyl group), 6.53 (s, 1H, vinyl group), 7.25 (d, 2H, benzene ring), 7.53 (t, 1H, benzene ring), 7.75 (m, 2H, benzene ring), 7.91 (s, 1H, amino group), 8.06 (d, 1H, benzene ring)

According to the above-mentioned analysis result, the obtained compound was proved to be the aimed compound, 1-methacrylamino-5-methacryloxynaphthalene.

(Evaluation Test 1)

Hereinafter, a liquid crystal cell of Example 1 practically produced according to Embodiment 1 will be described.

At first, a pair of substrates respectively having a transparent electrode on the surface were prepared and after the substrates were washed, an alignment film material was applied to both substrates to form a vertical alignment film of a polyimide. After the alignment film formation, the alignment film was pre-baked at 80° C. for 5 minutes and successively post-baked at 200° C. for 60 minutes. Thereafter, a sealing material was applied to one substrate and while ultraviolet rays being radiated at 5 J/cm$^2$, a liquid crystal composition containing a liquid crystal material having negative anisotropy of dielectric constant and a radical polymerizable monomer was dropped. The sealing material was temporarily hardened by dropping the liquid crystal composition while irradiating with ultraviolet rays. Thereafter, beads were dispersed as a spacer to the counter substrate and the substrates were stuck to each other and the sealing material was actually hardened by heating at 100° C.

In Example 1, a naphthalene compound represented by the following formula (9) was added as a radical polymerizable monomer in an amount of 0.25 weight % based on the entire liquid crystal composition. The compound represented by the following formula (9) was 1-methacrylamino-5-methacryloxynaphthalene obtained by the above-mentioned Synthesis Example.

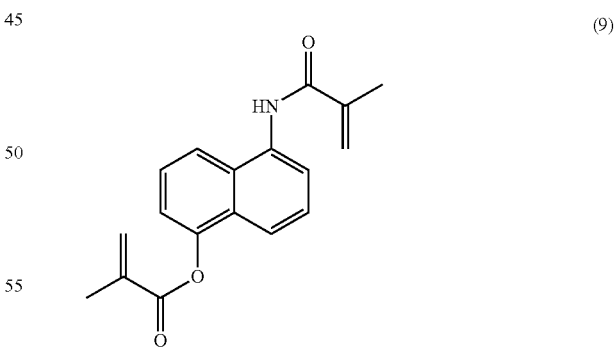

(9)

As comparative objects to Example 1, Comparative Examples 1 and 2 were produced. In Comparative Example 1, a compound represented by the following formula (10) was added as a radical polymerizable monomer in an amount of 0.25 weight % based on the entire liquid crystal composition. In Comparative Example 2, no radical polymerizable monomer was added.

(10)

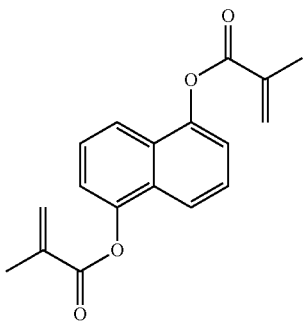

In the state that 10 V voltage was applied between transparent electrodes included in the upper and lower substrates, Example 1 and Comparative Examples 1 and 2 were irradiated with 2.57 mW/cm$^2$ of non-polarized ultraviolet rays from a normal direction for 20 minutes to polymerize the radical polymerizable monomers and to complete liquid crystal cells. A black light FHF-32BLB (wavelength region: 300 to 370 nm) manufactured by TOSHIBA Lighting & Technology Corporation was used as a light source for the non-polarized ultraviolet rays.

Regarding the completed respective liquid crystal cells, initial voltage holding ratio (VHR), voltage holding ratio (VHR) after an aging test, and remaining DC voltage after the aging test were measured for the respective liquid crystal cells. The aging test was carried out by leaving the cells in the environments of 45° C. and 90% humidity for 1000 hours.

The aging test was carried out in high temperature and high humidity environments and the voltage holding ratio (VHR) and the remaining DC voltage after the aging test were measured to evaluate the degree of occurrence of the above-mentioned stains and display unevenness. In the case where the voltage holding ratio (VHR) is high and the remaining DC voltage is low after the aging test, it can be said that such a liquid crystal display device can keep high display quality even in high temperature and high humidity environments.

The voltage holding ratio (VHR) was measured by using a 6254 model liquid crystal physical property measurement system manufactured by TOYO Corporation. At first, pulsed voltage was applied to between electrodes included in both substrates of each liquid crystal cell to electrically charge between electrodes. Thereafter, potential between electrodes was measured for 16.6 ms open period (period for applying no voltage) and the ratio of the electric charge retained was measured.

The remaining DC voltage was measured by applying 1V DC offset voltage to each liquid crystal cell for 10 hours and employing a flicker elimination method.

The following Table 1 represents the measurement results of the initial voltage holding ratio (initial VHR), voltage holding ratio (VHR) after the aging test, and remaining DC voltage after the aging test for Example 1 and Comparative Examples 1 and 2.

TABLE 1

| | Concentration of monomer based on entire liquid crystal composition | Initial VHR (%) | VHR(%) after aging test | Remaining DC voltage (mV) after aging test |
|---|---|---|---|---|
| Example 1 | Formula (9): 0.25(weight %) | 99.4 | 98.1 | 20 |
| Comparative Example 1 | Formula (10): 0.25(weight %) | 99.1 | 93.0 | 130 |
| Comparative Example 2 | No monomer addition (no polymer layer) | 99.4 | 93.2 | 170 |

In Example 1, the initial voltage holding ratio (initial VHR) was as high as 99% or higher and voltage holding ratio (VHR) after the aging test was not so much decreased and higher than that of Comparative Examples 1 and 2. The remaining DC voltage after the aging test for Example 1 represented a significantly-low value as compared with that for Comparative Examples 1 and 2. On the other hand, in Comparative Examples 1 and 2, the initial voltage holding ratio (initial VHR) was high but the voltage holding ratio (VHR) after the aging test was lowered to 93% level for both. The remaining DC voltage was 130 mV for Comparative Example 1 and 170 mV for Comparative Example 2 and so high for both.

According to the above-mentioned results, it is supposed that since having an amide group, the polymer layer (PSA layer) formed from the compound represented by the formula (9) of Example 1 formed hydrogen bonds with water, impurities, etc., penetrating the liquid crystal layer and accordingly, the voltage holding ratio (VHR) after the aging test was high and the remaining DC voltage was low.

On the other hand, it is supposed that although forming a polymer layer, the compound represented by the formula (10) used in Comparative Example 1 had no amide group and therefore failed to sufficiently form hydrogen bonds with water, impurities, etc., penetrating the liquid crystal layer and accordingly, the voltage holding ratio (VHR) after the aging test was lowered and high remaining DC voltage was generated. In Comparative Example 2, it is supposed that since water, impurities, etc., penetrate the liquid crystal layer, the voltage holding ratio (VHR) after the aging test was lowered and high remaining DC voltage was generated.

As described above, use of a monomer having an amide group and represented by the formula (9) makes it possible to obtain a liquid crystal display device capable of keeping high display quality even in high temperature and high humidity environments.

(Evaluation Test 2)

Hereinafter, liquid crystal cells of Examples 2 to 4 practically produced according to Embodiment 2 will be described. The production method for a liquid crystal cell employed in Evaluation Test 2 was the same as that in Evaluation Test 1, except that a monomer having a structure for producing a radical by hydrogen abstraction reaction by light irradiation or by self-cleavage reaction by light irradiation was added to a liquid crystal composition and that the light irradiation time for polymerizing the radical polymerizable monomer was changed to 10 minutes.

The liquid crystal cells produced in Evaluation Test 2 were obtained from the following Examples 2 to 4. In Examples 2 to 4, naphthalene compounds represented by the following formula (9) were added as a radical polymerizable monomer in an amount of 0.25 weight % based on the entire liquid crystal compositions, respectively.

In Examples 2 to 4, monomers having a structure for producing a radical by hydrogen abstraction reaction or self-cleavage reaction by light irradiation were added. In Example 2, a benzophenone compound represented by the following formula (11) was added in an amount of 0.05 weight %: in Example 3, a benzyl compound represented by the following formula (12) was added in an amount of 0.05 weight %: and in Example 4, a benzylketal compound represented by the following formula (13) was added in an amount of 0.05 weight % based on the entire liquid crystal compositions, respectively.

The compounds represented by the following formulas (11) and (12) are monomers having a structure for producing a radical by hydrogen abstraction reaction by light irradiation and the compound represented by the following formula (13) is a monomer having a structure for producing a radical by self-cleavage reaction by light irradiation.

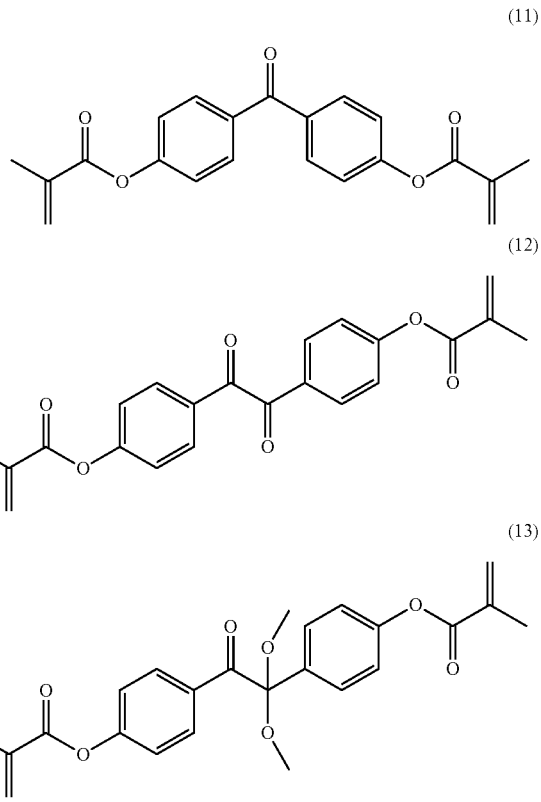

Regarding the completed respective liquid crystal cells, initial voltage holding ratio (VHR), voltage holding ratio (VHR) after an aging test, and remaining DC voltage after the aging test were measured for the respective liquid crystal cells. The measurement method for voltage holding ratio (VHR), the measurement method for remaining DC voltage, and the method for aging test were the same as those in Evaluation Test 1.

The following Table 2 represents the measurement results of the initial voltage holding ratio (initial VHR), voltage holding ratio (VHR) after the aging test, and remaining DC voltage after the aging test for Examples 2 to 4.

TABLE 2

| | Concentration of monomer based on entire liquid crystal composition | Initial VHR (%) | VHR(%) after aging test | Remaining DC voltage (mV) after aging test |
|---|---|---|---|---|
| Example 2 | Formula (9): 0.25(weight %) + Formula (11): 0.05(weight %) | 99.4 | 97.9 | 20 |
| Example 3 | Formula (9): 0.25(weight %) + Formula (12): 0.05(weight %) | 99.4 | 97.7 | 30 |
| Example 4 | Formula (9): 0.25(weight %) + Formula (13): 0.05(weight %) | 99.4 | 98 | 10 |

In all of Examples 2 and 4, the initial voltage holding ratio (initial VHR) was as high as 99% or higher and the voltage holding ratio (VHR) after the aging test was also a high value. In all of Examples 2 and 4, the remaining DC voltage was a low value.

From the above-mentioned results, a polymer layer can be formed by light irradiation within a short time by using a radical polymerizable monomer having an amide group represented by the above-mentioned formula (9) in combination with a monomer represented by the above-mentioned formulas (11) and (12) and having a structure for producing a radical by hydrogen abstraction reaction by light irradiation or a monomer represented by the above-mentioned formula (13) and having a structure for producing a radical by self-cleavage reaction by light irradiation. It is supposed that since having an amide group, the formed polymer layer formed hydrogen bonds with water, impurities, etc., penetrating the liquid crystal layer and accordingly, the voltage holding ratio (VHR) after the aging test was high and the remaining DC voltage was low.

As described above, a liquid crystal display device capable of keeping high display quality even in high temperature and high humidity environments was obtained by using a monomer having an amide group as represented by the above-mentioned formula (9) in combination with a monomer having a structure for producing a radical by hydrogen abstraction reaction by light irradiation or a monomer having a structure for producing a radical by self-cleavage reaction by light irradiation.

(Evaluation Test 3)

Hereinafter, a liquid crystal cell of Example 5 practically produced according to Embodiment 1 will be described. The production method for a liquid crystal cell employed in Evaluation Test 3 is the same as that employed in Evaluation Test 1, except that a polyimide horizontal alignment film with low imidation ratio was formed on the substrates and that a liquid crystal material with positive anisotropy of dielectric constant was used.

In Example 5, a naphthalene compound represented by the above-mentioned formula (9) was added as a radical polymerizable monomer in an amount of 0.25 weight % based on the entire liquid crystal composition.

As comparative objects to Examples, Comparative Examples 3 and 4 were produced. In Comparative Example 3, a compound represented by the above-mentioned formula (10) was added as a radical polymerizable monomer in an amount of 0.25 weight % based on the entire liquid crystal composition. In Comparative Example 4, no radical polymerizable monomer was added.

Regarding the completed respective liquid crystal cells, initial voltage holding ratio (VHR), voltage holding ratio (VHR) after an aging test, and remaining DC voltage after the aging test were measured for the respective liquid crystal cells. The measurement method for voltage holding ratio (VHR), the measurement method for remaining DC voltage, and the method for aging test were the same as those in Evaluation Test 1.

The following Table 3 represents the measurement results of the initial voltage holding ratio (initial VHR), voltage holding ratio (VHR) after the aging test, and remaining DC voltage after the aging test for Example 5 and Comparative Examples 3 and 4.

TABLE 3

| | Concentration of monomer based on entire liquid crystal composition | Initial VHR (%) | VHR(%) after aging test | Remaining DC voltage (mV) after aging test |
|---|---|---|---|---|
| Example 5 | Formula (9): 0.25(weight %) | 98.4 | 97.0 | 0 |
| Comparative Example 3 | Formula (10): 0.25(weight %) | 98.3 | 92.5 | 120 |
| Comparative Example 4 | No monomer addition (no polymer layer) | 96.5 | 90.1 | 170 |

In Example 5, the initial voltage holding ratio (initial VHR) was as high as 98% or higher, and voltage holding ratio (VHR) after the aging test was not so much decreased and higher than that of Comparative Examples 3 and 4. The remaining DC voltage after the aging test for Example 5 represented a significantly-low value as compared with that for Comparative Examples 3 and 4. On the other hand, in Comparative Examples 3 and 4, the initial voltage holding ratio (initial VHR) was high but the voltage holding ratio (VHR) after the aging test was lowered to 92% level for Comparative Example 3 and to 90% level for Comparative Example 4. The remaining DC voltage was 120 mV for Comparative Example 3 and 170 mV for Comparative Example 4 and so high for both.

According to the above-mentioned results, it is supposed that since having an amide group, the polymer layer (PSA layer) formed from the compound represented by the formula (9) of Example 5 formed hydrogen bonds with water, impurities, etc., penetrating the liquid crystal layer and accordingly, the voltage holding ratio (VHR) after the aging test is high and the remaining DC voltage is low.

On the other hand, it is supposed that although forming a polymer layer, the compound represented by the formula (10) used in Comparative Example 3 had no amide group and therefore failed to sufficiently form hydrogen bonds with water, impurities, etc., penetrating the liquid crystal layer and accordingly, the voltage holding ratio (VHR) after the aging test was lowered and high remaining DC voltage was generated. In Comparative Example 4, it is supposed that since water, impurities, etc., penetrated the liquid crystal layer, the voltage holding ratio (VHR) after the aging test was lowered and high remaining DC voltage was generated.

As described above, even in the case where a polyamic acid alignment film, that is, a polyimide horizontal alignment film with low imidation ratio, is used, use of a monomer having an amide group and represented by the formula (9) makes it possible to obtain a liquid crystal display device capable of keeping high display quality even in high temperature and high humidity environments.

(Evaluation Test 4)

Hereinafter, liquid crystal cells of Examples 6 to 8 practically produced according to Embodiment 2 will be described. The production method for a liquid crystal cell employed in Evaluation Test 4 was the same as that in Evaluation Test 3, except that a monomer having a structure for producing a radical by hydrogen abstraction reaction by light irradiation or by self-cleavage reaction by light irradiation was added to a liquid crystal composition and that the light irradiation time for polymerizing the radical polymerizable monomer was changed to 10 minutes.

The liquid crystal cells produced in Evaluation Test 4 were obtained from the following Examples 6 to 8. In Examples 6 to 8, naphthalene compounds represented by the above-mentioned formula (9) were added as a radical polymerizable monomer in an amount of 0.25 weight % based on the entire liquid crystal compositions, respectively.

In Examples 6 to 8, monomers having a structure for producing a radical by hydrogen abstraction reaction or self-cleavage reaction by light irradiation were added. In Example 6, a benzophenone compound represented by the above-mentioned formula (11) was added in an amount of 0.05 weight %: in Example 7, a benzyl compound represented by the above-mentioned formula (12) was added in an amount of 0.05 weight %: and in Example 8, a benzylketal compound represented by the above-mentioned formula (13) was added in an amount of 0.05 weight % based on the entire liquid crystal compositions, respectively.

The compounds represented by the above-mentioned formulas (11) and (12) are monomers having a structure for producing a radical by hydrogen abstraction reaction by light irradiation and the compound represented by the above-mentioned formula (13) is a monomer having a structure for producing a radical by self-cleavage reaction by light irradiation.

Regarding the completed respective liquid crystal cells, initial voltage holding ratio (VHR), voltage holding ratio (VHR) after an aging test, and remaining DC voltage after the aging test were measured for the respective liquid crystal cells. The measurement method for voltage holding ratio (VHR), the measurement method for remaining DC voltage, and the method for aging test were the same as those in Evaluation Test 1.

The following Table 4 represents the measurement results of the initial voltage holding ratio (initial VHR), voltage holding ratio (VHR) after the aging test, and remaining DC voltage after the aging test for Examples 6 to 8.

TABLE 4

| | Concentration of monomer based on entire liquid crystal composition | Initial VHR (%) | VHR(%) after aging test | Remaining DC voltage (mV) after aging test |
|---|---|---|---|---|
| Example 6 | Formula (9): 0.25(weight %) + Formula (11): 0.05(weight %) | 98.6 | 97.0 | 10 |
| Example 7 | Formula (9): 0.25(weight %) + Formula (12): 0.05(weight %) | 98.5 | 96.5 | 30 |
| Example 8 | Formula (9): 0.25(weight %) + Formula (13): 0.05(weight %) | 98.7 | 97.1 | 0 |

In all of Examples 6 to 8, the initial voltage holding ratio (initial VHR) was as high as 98% or higher and the voltage holding ratio (VHR) after the aging test was not so much lowered. In all of Examples 6 and 8, the remaining DC voltage was a low value.

From the above-mentioned results, a polymer layer can be formed by light irradiation within a short time by using a radical polymerizable monomer having an amide group represented by the above-mentioned formula (9) in combination with a monomer represented by the above-mentioned chemical formulas (11) and (12) and having a structure for producing a radical by hydrogen abstraction reaction by light irradiation or a monomer represented by the above-mentioned formula (13) and having a structure for producing a radical by self-cleavage reaction by light irradiation. It is supposed that since having an amide group, the formed polymer layer formed hydrogen bonds with water, impurities, etc., penetrating the liquid crystal layer and accordingly, the voltage holding ratio (VHR) after the aging test was high and the remaining DC voltage was low.

As described above, a liquid crystal display device capable of keeping high display quality even in high temperature and high humidity environments was obtained by using a monomer having an amide group as represented by the above-mentioned formula (9) in combination with a monomer having a structure for producing a radical by hydrogen abstraction reaction by light irradiation or a monomer having a structure for producing a radical by self-cleavage reaction by light irradiation.

According to the results of Evaluation Tests 1 to 4, a liquid crystal display device capable of keeping high display quality even in high temperature and high humidity environments can be obtained by using either a vertical alignment film or a horizontal alignment film. Further, a liquid crystal display device capable of keeping high display quality even in high temperature and high humidity environments can be obtained by using a liquid crystal material with positive anisotropy of dielectric constant and a liquid crystal material with negative anisotropy of dielectric constant.

REFERENCE SIGNS LIST 103, 203 Sealing material
104, 204 (First) radical polymerizable monomer
105, 205 Liquid crystal layer
206 (Second) radical polymerizable monomer
107, 207 Polymer layer (PSA layer)
108, 208 Alignment film
110, 210 Array substrate
120, 220 Color filter substrate

The invention claimed is:

1. A liquid crystal composition comprising:
a liquid crystal material;
a first monomer represented by the following chemical formula (2); and
a second monomer being at least one of a compound represented by the following chemical formulas (6-1) to (6-8) and having a structure producing a radical by hydrogen abstraction reaction by light irradiation, and a compound represented by the following chemical formula (7) and having a structure producing a radical by self-cleavage reaction by light irradiation;

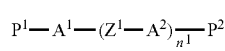

(2)

where, in the chemical formula (2):

$A^1$ denotes a divalent alicyclic, aromatic monocyclic, or condensed polycyclic hydrocarbon group;

$A^2$ denotes a phenylene group;

a —$CH_2$— group included in $A^1$ and $A^2$ may be substituted with an —O— or a —S— group unless neighboring each other;

a —CH= group included in $A^1$ and $A^2$ may be substituted with a —N= group unless neighboring each other;

a hydrogen atom included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^1$ denotes —O—, —CO—, —COO—, —OCO—, —NRCO—, —CONR— groups, or a direct bond;

R denotes a hydrogen atom, or a straight alkyl or alkenyl group with 1 to 6 carbon atoms;

$P^1$ and $P^2$ each denote a radical polymerizable group, one of $P^1$ and $P^2$ is an acryloylamino or a methacryloylamino group, and the other of $P^1$ and $P^2$ is an acryloyl or a methacryloyl group; and $n^1$ denotes 0 or 1,

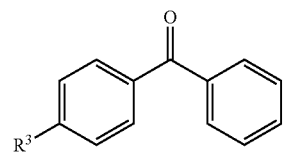

(6-1)

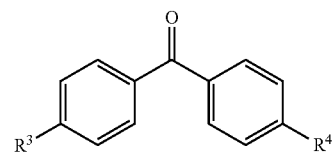

(6-2)

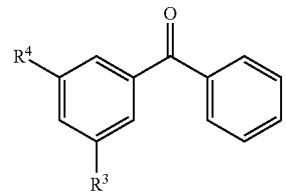

(6-3)

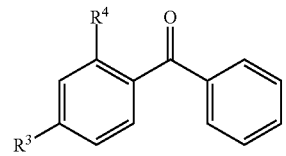

(6-4)

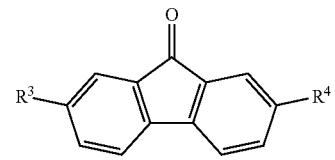

(6-5)

-continued (6-6)
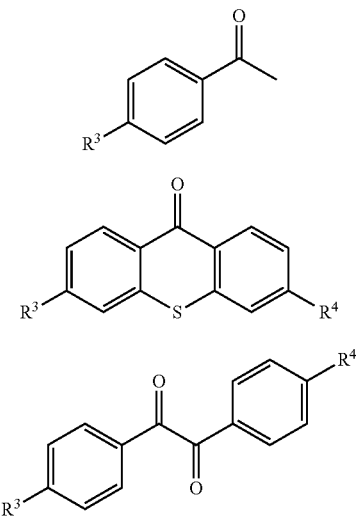
(6-7)

(6-8)

where, in the chemical formulas (6-1) to (6-8):
$R^3$ and $R^4$ may be the same or different, and denote a -$Sp^8$-P group, a hydrogen atom, a halogen atom, —CN, —$NO_2$, —NCO, —NCS, —OCN, —SCN, —$SF_5$, or a straight or branched alkyl or aralkyl with 1 to 12 carbon atoms, or phenyl group;
at least one of $R^3$ and $R^4$ contains a -$Sp^8$-P group;
P denotes a radical polymerizable group;
$Sp^8$ denotes a straight, branched or cyclic alkylene or alkyleneoxy group with 1 to 6 carbon atoms, or a direct bond;
in the case where at least one of $R^3$ and $R^4$ is an alkyl or aralkyl with 1 to 12 carbon atoms or phenyl group, a hydrogen atom included in $R^3$ and $R^4$ may be substituted with a fluorine atom, a chlorine atom, or a -$Sp^8$-P group; and
a —$CH_2$— group included in $R^3$ and $R^4$ may be substituted with —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH═CH—, —CF═CF—, —C≡C—, —CH═CH—COO—, or —OCO—CH═CH— group unless an oxygen atom, a sulfur atom, and a nitrogen atom neighbor one another, (7)
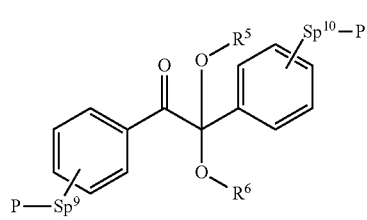

where, in the chemical formula (7):
$R^5$ denotes a straight or branched alkyl or alkenyl group with 1 to 4 carbon atoms;
$R^6$ denotes a straight or branched alkyl or alkenyl group with 1 to 4 carbon atoms;

P denotes the same or different radical polymerizable group;
$Sp^5$ denotes a straight, branched, or cyclic alkylene, alkyleneoxy, or alkylenecarbonyloxy group with 1 to 6 carbon atoms, or a direct bond; and
$Sp^{10}$ denotes a straight, branched, or cyclic alkylene, alkyleneoxy, or alkylenecarbonyloxy group with 1 to 6 carbon atoms, or a direct bond, wherein
the compound having a structure producing a radical by hydrogen abstraction reaction by light irradiation is a compound represented by the following chemical formulas (11) or (12); and
the compound having a structure producing a radical by self-cleavage reaction by light irradiation is a compound represented by the following chemical formula (13):

(11)
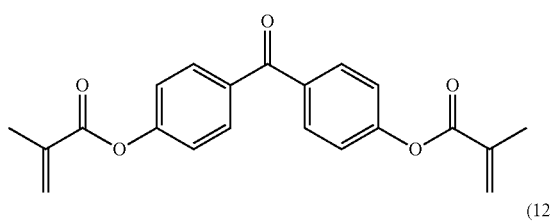

(12)
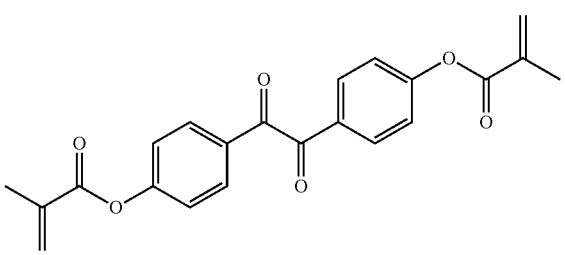

(13)
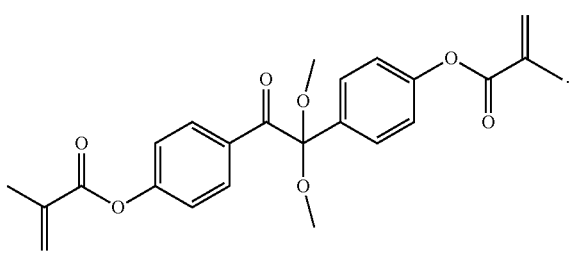

2. A liquid crystal display device comprising:
a pair of substrates;
a liquid crystal layer containing a liquid crystal material and sandwiched between the pair of the substrates; and
a polymer layer defined on at least one of the pair of substrates that controls alignment of liquid crystal molecules, the polymer layer being defined by polymerizing one or more kinds of monomers, the monomers including:
a first monomer represented by the following chemical formula (2); and
a second monomer being at least one of a compound represented by the following chemical formulas (6-1) to (6-8) and having a structure producing a radical by hydrogen abstraction reaction by light irradiation, and a compound represented by the following chemical formula (7) and having a structure producing a radical by self-cleavage reaction by light irradiation;

$$P^1\text{—}A^1\text{—}(Z^1\text{—}A^2)_{n^1}\text{—}P^2 \quad (2)$$

where, in the chemical formula (2):
A$^1$ denotes a divalent alicyclic, aromatic monocyclic, or condensed polycyclic hydrocarbon group;
A$^2$ denotes a phenylene group;
a —CH$_2$— group included in A$^1$ and A$^2$ may be substituted with an —O— or a —S— group unless neighboring each other;
a —CH= group included in A$^1$ and A$^2$ may be substituted with a —N= group unless neighboring each other;
a hydrogen atom included in A$^1$ and A$^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;
Z$^1$ denotes —O—, —CO—, —COO—, —OCO—, —NRCO—, —CONR— groups, or a direct bond;
R denotes a hydrogen atom, or a straight alkyl or alkenyl group with 1 to 6 carbon atoms;
P$^1$ and P$^2$ each denote a radical polymerizable group, one of P$^1$ and P$^2$ is an acryloylamino or a methacryloylamino group, and the other of P$^1$ and P$^2$ is an acryloyl or a methacryloyl group; and
n$^1$ denotes 0 or 1, (6-1)

(6-2)

(6-3)

(6-4)

(6-5)

(6-6)

(6-7)

(6-8)

where, in the chemical formulas (6-1) to (6-8):
R$^3$ and R$^4$ may be the same or different, and denote a -Sp$^8$-P group, a hydrogen atom, a halogen atom, —CN, —NO$_2$, —NCO, —NCS, —OCN, —SCN, —SF$_5$, or a straight or branched alkyl or aralkyl with 1 to 12 carbon atoms, or phenyl group;
at least one of R$^3$ and R$^4$ contains a -Sp$^8$-P group;
P denotes a radical polymerizable group;
Sp$^8$ denotes a straight, branched or cyclic alkylene or alkyleneoxy group with 1 to 6 carbon atoms, or a direct bond;
in the case where at least one of R$^3$ and R$^4$ is an alkyl or aralkyl with 1 to 12 carbon atoms or phenyl group, a hydrogen atom included in R$^3$ and R$^4$ may be substituted with a fluorine atom, a chlorine atom, or a -Sp$^8$-P group; and
a —CH$_2$— group included in R$^3$ and R$^4$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, or —OCO—CH=CH— group unless an oxygen atom, a sulfur atom, and a nitrogen atom neighbor one another, (7)

where, in the chemical formula (7):
R$^5$ denotes a straight or branched alkyl or alkenyl group with 1 to 4 carbon atoms;
R$^6$ denotes a straight or branched alkyl or alkenyl group with 1 to 4 carbon atoms;

P denotes the same or different radical polymerizable group;

$Sp^9$ denotes a straight, branched, or cyclic alkylene, alkyleneoxy, or alkylenecarbonyloxy group with 1 to 6 carbon atoms, or a direct bond; and $Sp^{10}$ denotes a straight, branched, or cyclic alkylene, alkyleneoxy, or alkylenecarbonyloxy group with 1 to 6 carbon atoms, or a direct bond, wherein the compound having a structure producing a radical by hydrogen abstraction reaction by light irradiation is a compound represented by the following chemical formulas (11) or (12); and the compound having a structure producing a radical by self-cleavage reaction by light irradiation is a compound represented by the following chemical formula (13):

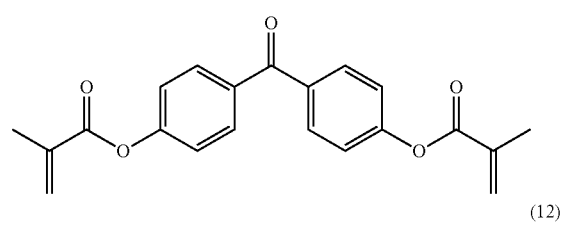
(11)

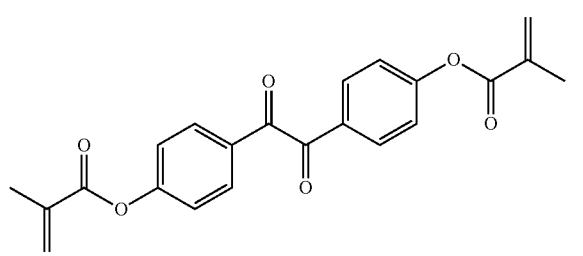
(12)

(13)

3. A production method for a liquid crystal display device comprising:
injecting a liquid crystal composition containing a liquid crystal material and one or more kinds of monomers between a pair of substrates; and
forming a polymer layer that controls alignment of liquid crystal molecules on the pair of substrates by irradiating the liquid crystal composition with light and thereby polymerizing the monomers, the monomers including:
a first monomer represented by the following chemical formula (2); and
a second monomer being at least one of a compound represented by the following chemical formulas (6-1) to (6-8) and having a structure producing a radical by hydrogen abstraction reaction by light irradiation, and a compound represented by the following chemical formula (7) and having a structure producing a radical by self-cleavage reaction by light irradiation;

$$P^1-A^1-(Z^1-A^2)_{n^1}-P^2 \quad (2)$$

where, in the chemical formula (2):

$A^1$ denotes a divalent alicyclic, aromatic monocyclic, or condensed polycyclic hydrocarbon group;

$A^2$ denotes a phenylene group;

a —$CH_2$— group included in $A^1$ and $A^2$ may be substituted with an —O— or a —S— group unless neighboring each other;

a —CH= group included in $A^1$ and $A^2$ may be substituted with a —N= group unless neighboring each other;

a hydrogen atom included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^1$ denotes —O—, —CO—, —COO—, —OCO—, —NRCO—, —CONR— groups, or a direct bond;

R denotes a hydrogen atom, or a straight alkyl or alkenyl group with 1 to 6 carbon atoms;

$P^1$ and $P^2$ each denote a radical polymerizable group, one of $P^1$ and $P^2$ is an acryloylamino or a methacryloylamino group, and the other of $P^1$ and $P^2$ is an acryloyl or a methacryloyl group; and $n^1$ denotes 0 or 1,

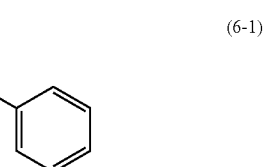
(6-1)

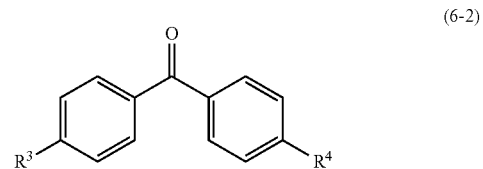
(6-2)

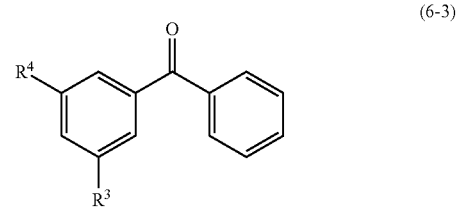
(6-3)

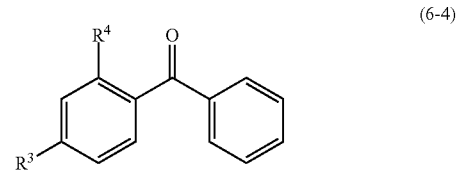
(6-4)

-continued (6-5)
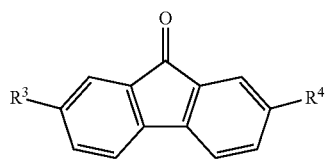

(6-6)
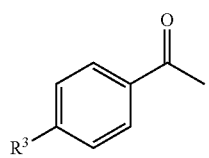

(6-7)
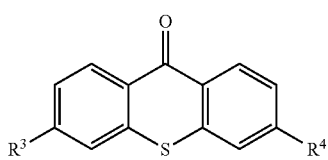

(6-8)
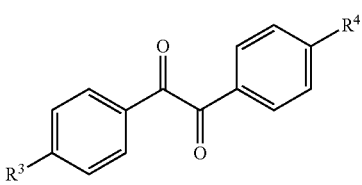

where, in the chemical formulas (6-1) to 6-8):
$R^3$ and $R^4$ may be the same or different, and denote a -$Sp^8$-P group, a hydrogen atom, a halogen atom, —CN, —$NO_2$, —NCO, —NCS, —OCN, —SCN, —$SF_5$, or a straight or branched alkyl or aralkyl with 1 to 12 carbon atoms, or phenyl group;

at least one of $R^3$ and $R^4$ contains a -$Sp^8$-P group;

P denotes a radical polymerizable group;

$Sp^8$ denotes a straight, branched or cyclic alkylene or alkyleneoxy group with 1 to 6 carbon atoms, or a direct bond;

in the case where at least one of $R^3$ and $R^4$ is an alkyl or aralkyl with 1 to 12 carbon atoms or phenyl group, a hydrogen atom included in $R^3$ and $R^4$ may be substituted with a fluorine atom, a chlorine atom, or a -$Sp^8$-P group; and a —$CH_2$— group included in $R^3$ and $R^4$ may be substituted with —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH═CH—, —CF═CF—, —C≡C—, —CH═CH—COO—, or —OCO—CH═CH— group unless an oxygen atom, a sulfur atom, and a nitrogen atom neighbor one another, (7)
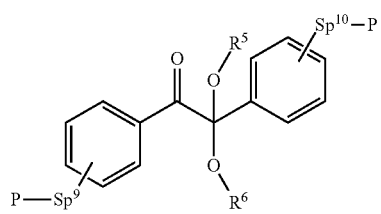

where, in the chemical formula (7):
$R^5$ denotes a straight or branched alkyl or alkenyl group with 1 to 4 carbon atoms;
$R^6$ denotes a straight or branched alkyl or alkenyl group with 1 to 4 carbon atoms;
P denotes the same or different radical polymerizable group;
$Sp^9$ denotes a straight, branched, or cyclic alkylene, alkyleneoxy, or alkylenecarbonyloxy group with 1 to 6 carbon atoms, or a direct bond; and
$Sp^{10}$ denotes a straight, branched, or cyclic alkylene, alkyleneoxy, or alkylenecarbonyloxy group with 1 to 6 carbon atoms, or a direct bond, wherein
the compound having a structure producing a radical by hydrogen abstraction reaction by light irradiation is a compound represented by the following chemical formulas (11) or (12); and
the compound having a structure producing a radical by self-cleavage reaction by light irradiation is a compound represented by the following chemical formula (13):

(11)
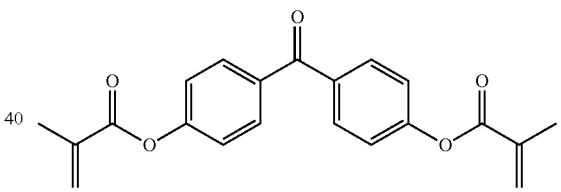

(12)
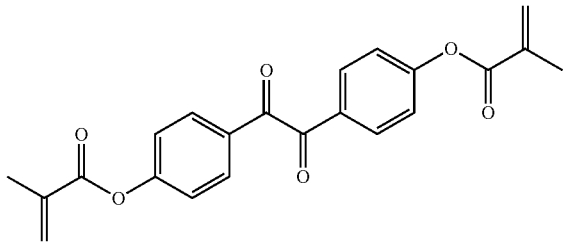

(13)
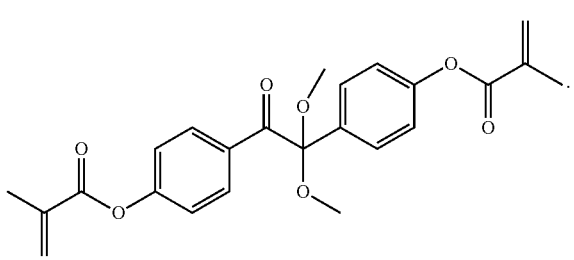

4. The liquid crystal composition according to claim 1, wherein the first monomer represented by the chemical formula (2) is a compound represented by one of the following formulas (5-1)-(5-5), (5-10), (5-12), (5-14), (5-16), and (5-18):
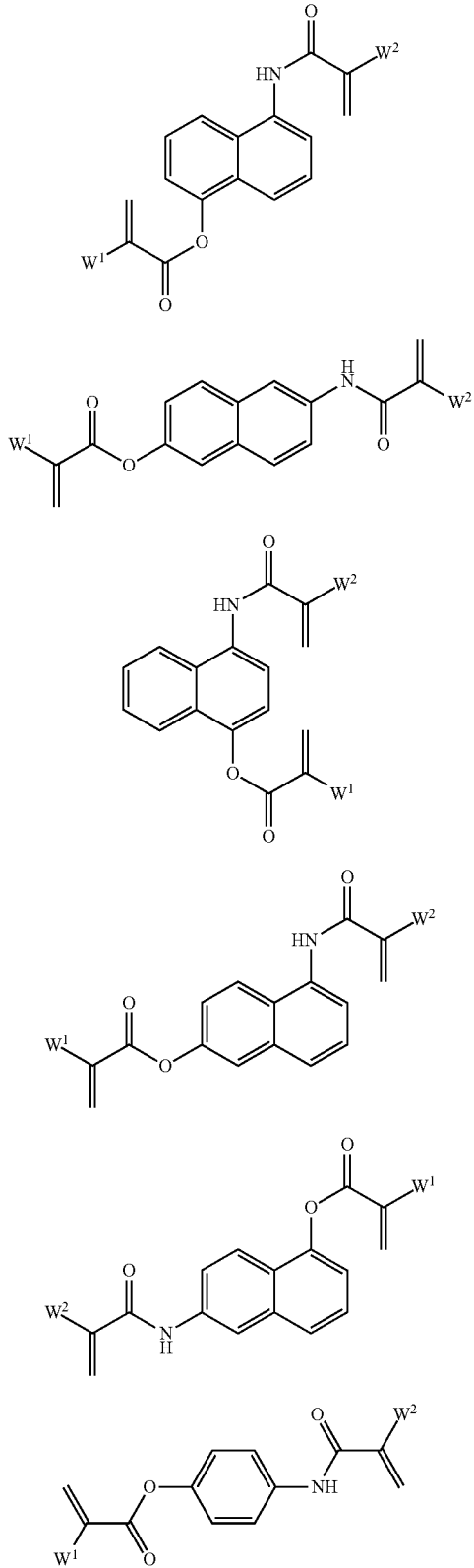
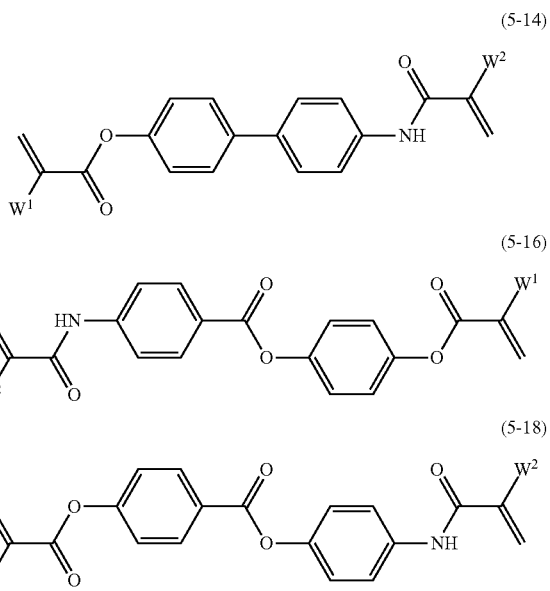
where, in the chemical formulas (5-1)-(5-5), (5-10), (5-12), (5-14), (5-16), and (5-18):
$W^1$ and $W^2$ may be the same or different, and denote —H or —$CH_3$ group.
5. The liquid crystal composition according to claim 1, wherein the first monomer represented by the chemical formula (2) is a compound represented by one of the following chemical formulas (5-1)-(5-5):
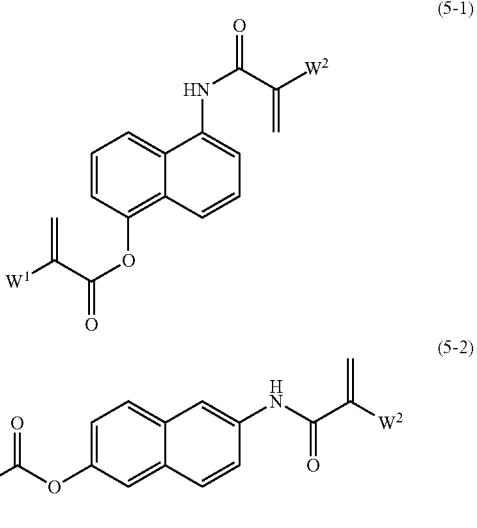

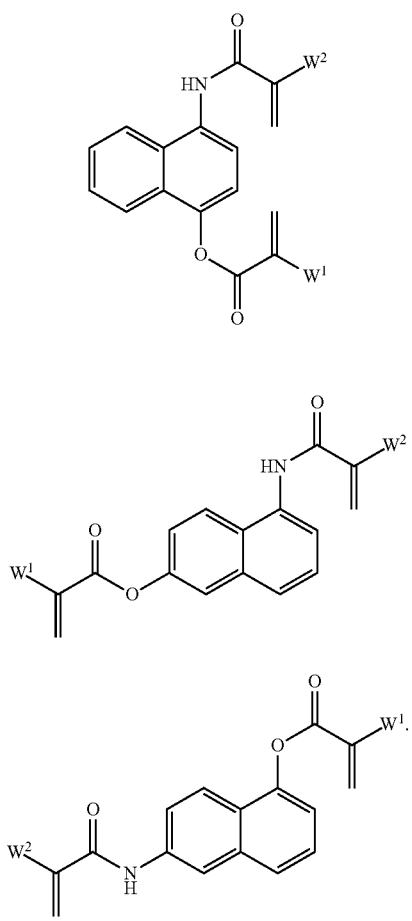
6. The liquid crystal display device according to claim 2, wherein the first monomer represented by the chemical formula (2) is a compound represented by one of the following chemical formulas (5-1)-(5-5), (5-10), (5-12), (5-14), (5-16), and (5-18):
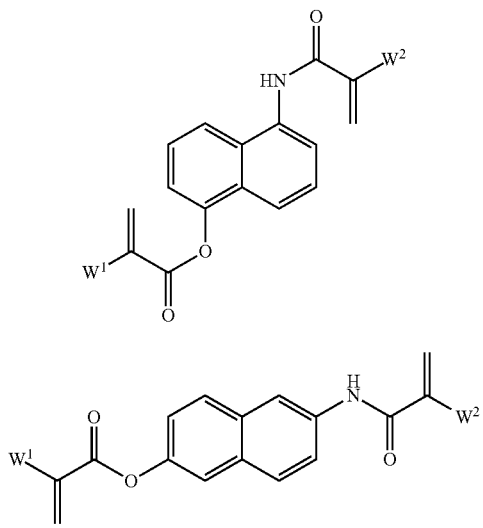
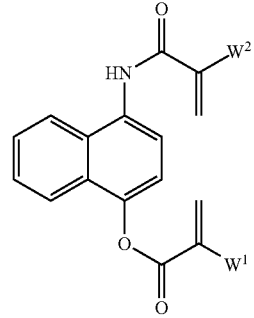
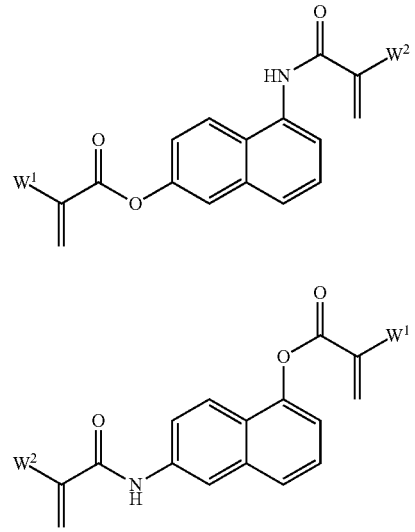
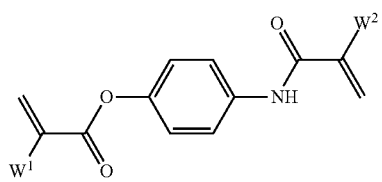
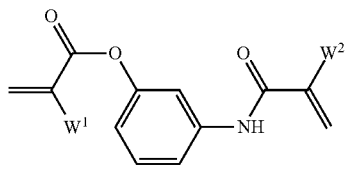
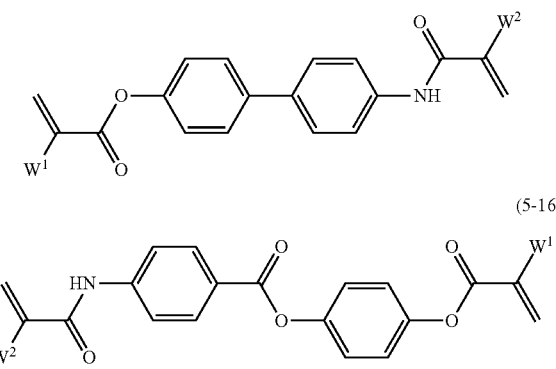

(5-18)

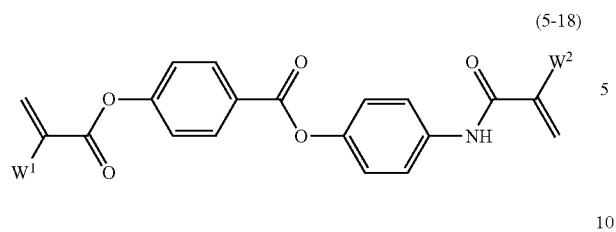

where, in the formulas (5-1)-(5-5), (5-10), (5-12), (5-14), (5-16), and (5-18):

$W^1$ and $W^2$ may be the same or different, and denote —H or —$CH_3$ group.

7. The liquid crystal display device according to claim 2, wherein the first monomer represented by the chemical formula (2) is a compound represented by one of the following chemical formulas (5-1)-(5-5):

(5-1)

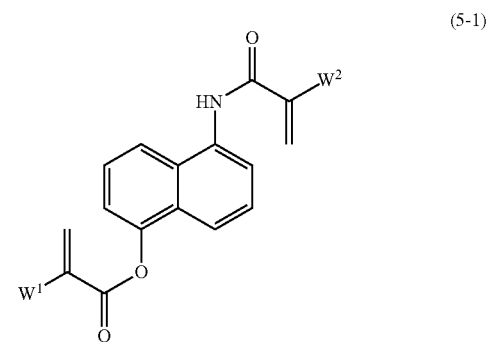

(5-2)

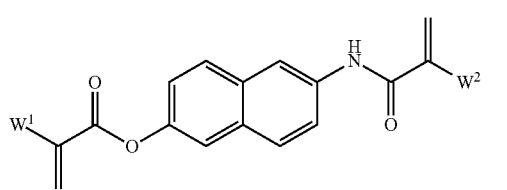

(5-3)

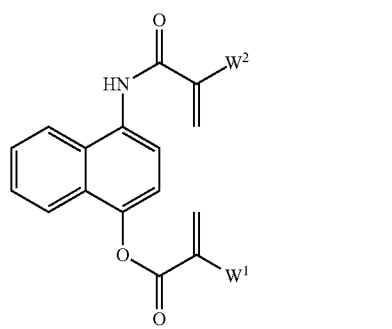

(5-4)

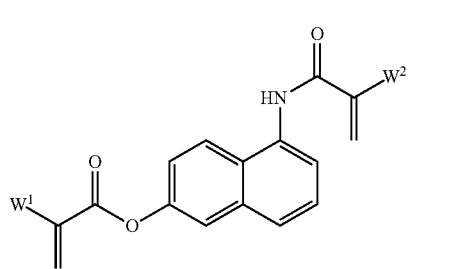

(5-5)

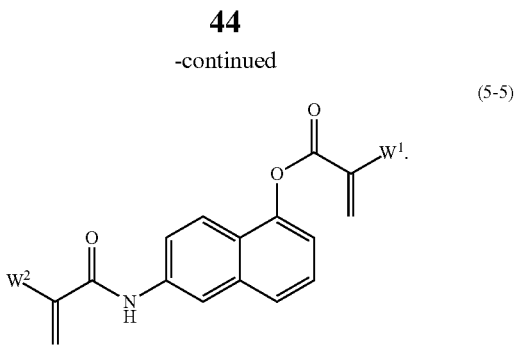

8. The production method for a liquid crystal display device according to claim 3, wherein the first monomer represented by the chemical formula (2) is a compound represented by one of the following chemical formulas (5-1)-(5-5), (5-10), (5-12), (5-14), (5-16), and (5-18):

(5-1)

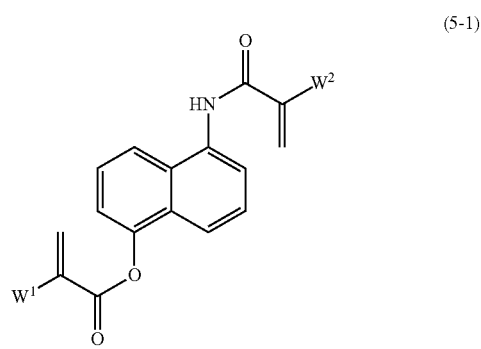

(5-2)

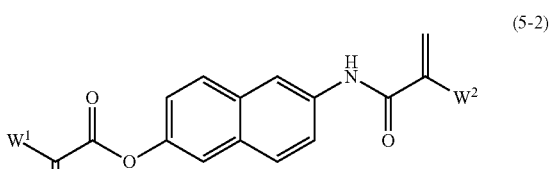

(5-3)

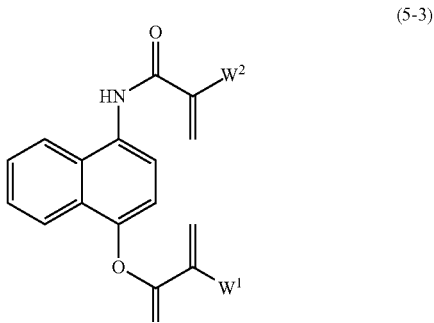

(5-4)

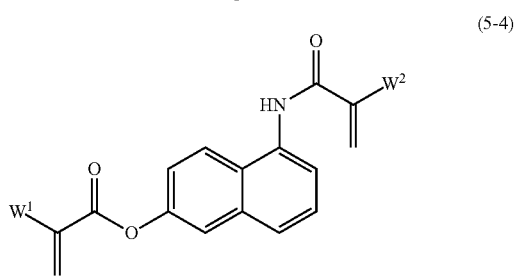

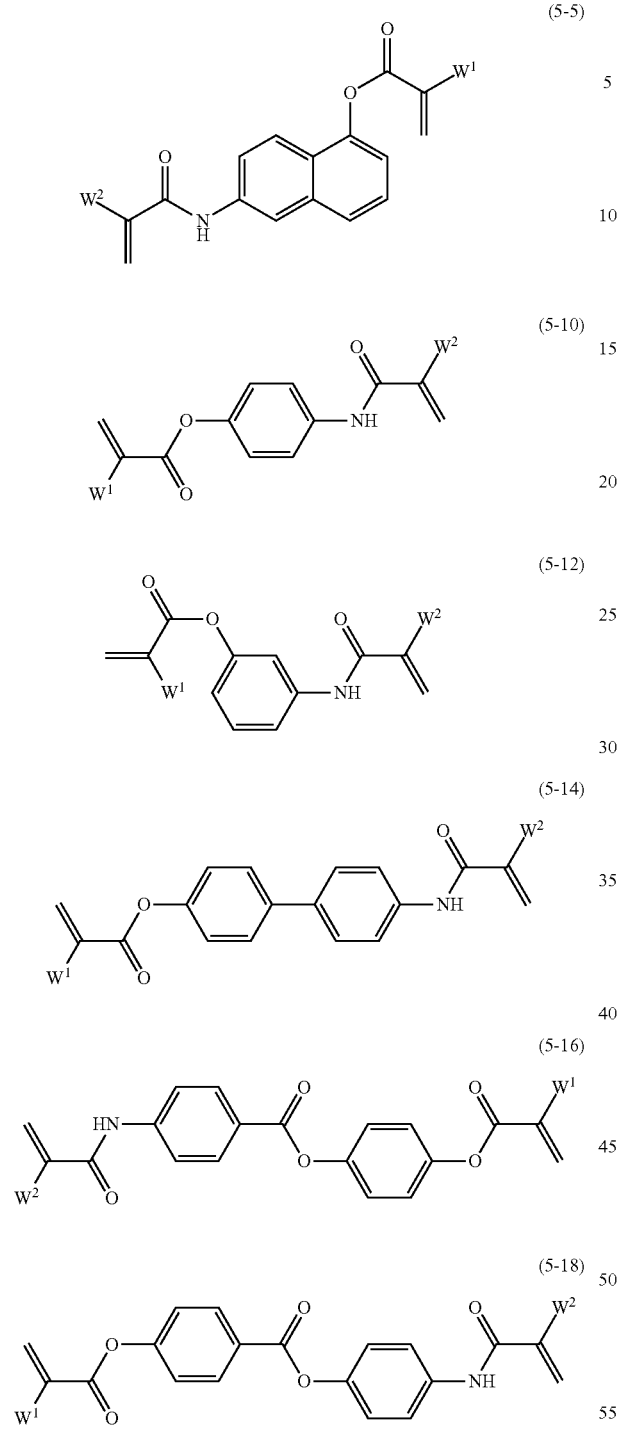
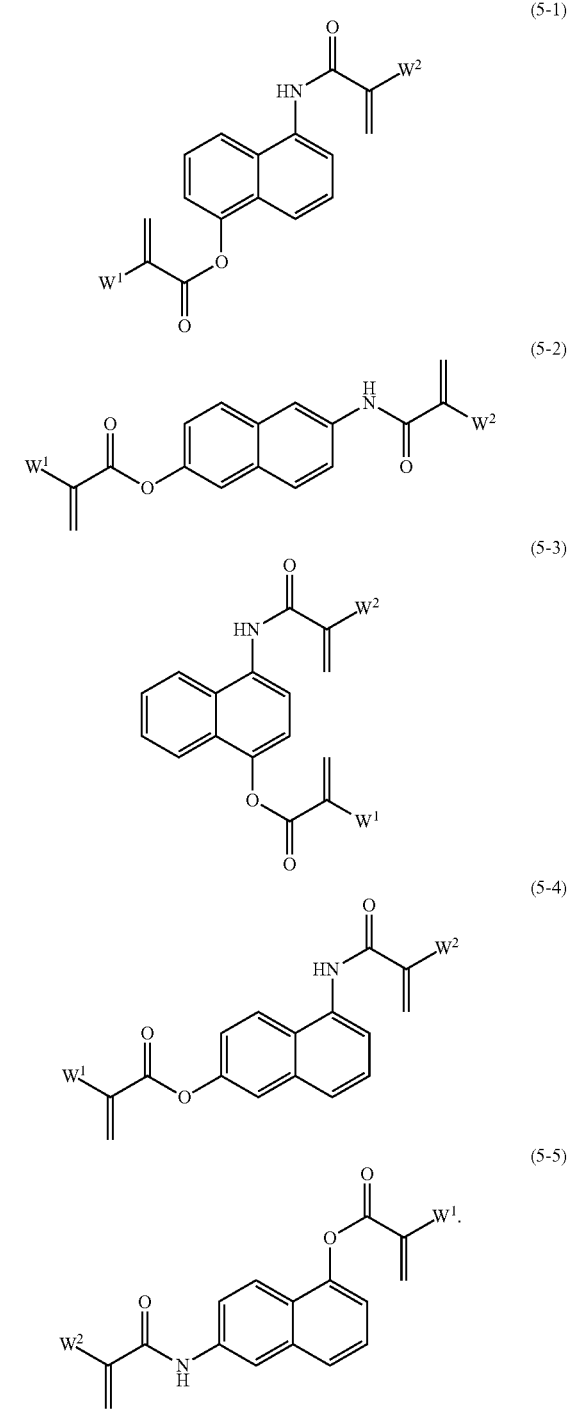

where, in the chemical formulas (5-1)-(5-5), (5-10), (5-12), (5-14), (5-16), and (5-18):

$W^1$ and $W^2$ may be the same or different, and denote —H or —$CH_3$ group.

9. The production method for a liquid crystal display device according to claim 3, wherein the first monomer represented by the chemical formula (2) is a compound represented by one of the following chemical formulas (5-1)-(5-5):

10. A liquid crystal composition comprising:
a liquid crystal material;
a first monomer represented by the following chemical formula (2); and
a second monomer being at least one of a compound represented by the following chemical formulas (6-1) to (6-8) and having a structure producing a radical by hydrogen abstraction reaction by light irradiation, and a compound represented by the following chemical formula (7) and having a structure producing a radical by self-cleavage reaction by light irradiation;

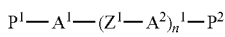 (2)

where, in the chemical formula (2):
$A^1$ denotes a divalent alicyclic, aromatic monocyclic, or condensed polycyclic hydrocarbon group;
$A^2$ denotes a phenylene group;
a —$CH_2$— group included in $A^1$ and $A^2$ may be substituted with an —O— or a —S— group unless neighboring each other;
a —CH= group included in $A^1$ and $A^2$ may be substituted with a —N= group unless neighboring each other;
a hydrogen atom included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;
$Z^1$ denotes —O—, —CO—, —COO—, —OCO—, —NRCO—, —CONR— groups, or a direct bond;
R denotes a hydrogen atom, or a straight alkyl or alkenyl group with 1 to 6 carbon atoms;
$P^1$ and $P^2$ each denote a radical polymerizable group, one of $P^1$ and $P^2$ is an acryloylamino or a methacryloylamino group, and the other of $P^1$ and $P^2$ is an acryloyl or a methacryloyl group; and
$n^1$ denotes 0 or 1, (6-1)

(6-2)

(6-3)

(6-4)

(6-5)

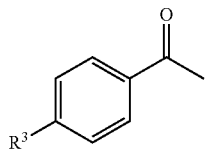 (6-6)

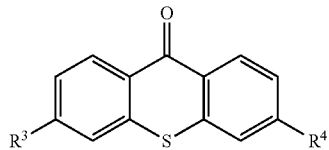 (6-7)

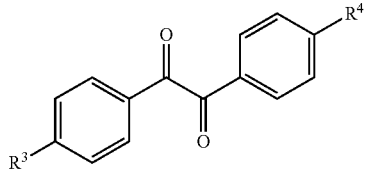 (6-8)

where, in the chemical formulas (6-1) to (6-8):
$R^3$ and $R^4$ may be the same or different, and denote a -$Sp^8$-P group, a hydrogen atom, a halogen atom, —CN, —$NO_2$, —NCO, —NCS, —OCN, —SCN, —$SF_5$, or a straight or branched alkyl or aralkyl with 1 to 12 carbon atoms, or phenyl group;
at least one of $R^3$ and $R^4$ contains a -$Sp^8$-P group;
P denotes a radical polymerizable group;
$Sp^8$ denotes a straight, branched or cyclic alkylene or alkyleneoxy group with 1 to 6 carbon atoms, or a direct bond;
in the case where at least one of $R^3$ and $R^4$ is an alkyl or aralkyl with 1 to 12 carbon atoms or phenyl group, a hydrogen atom included in $R^3$ and $R^4$ may be substituted with a fluorine atom, a chlorine atom, or a -$Sp^8$-P group; and
a —$CH_2$— group included in $R^3$ and $R^4$ may be substituted with —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH=CH—, —CF=CF—, —C≡C—, —CH=CH—COO—, or —OCO—CH=CH— group unless an oxygen atom, a sulfur atom, and a nitrogen atom neighbor one another,

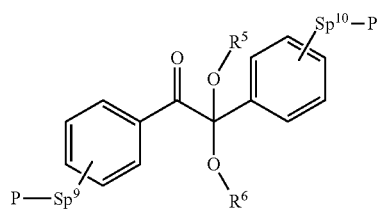 (7)

where, in the chemical formula (7):
$R^5$ denotes a straight or branched alkyl or alkenyl group with 1 to 4 carbon atoms;
$R^6$ denotes a straight or branched alkyl or alkenyl group with 1 to 4 carbon atoms;

P denotes the same or different radical polymerizable group;

$Sp^5$ denotes a straight, branched, or cyclic alkylene, alkyleneoxy, or alkylenecarbonyloxy group with 1 to 6 carbon atoms, or a direct bond; and $Sp^{10}$ denotes a straight, branched, or cyclic alkylene, alkyleneoxy, or alkylenecarbonyloxy group with 1 to 6 carbon atoms, or a direct bond, wherein the first monomer represented by the chemical formula (2) is a compound represented by one of the following chemical formulas (5-10), (5-12), (5-16), and (5-18):

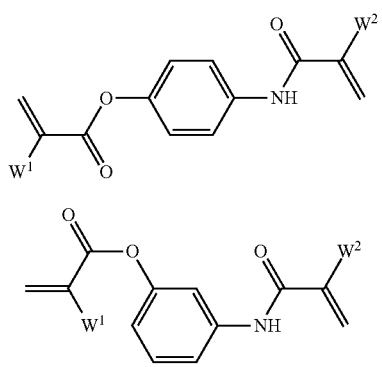
(5-10)

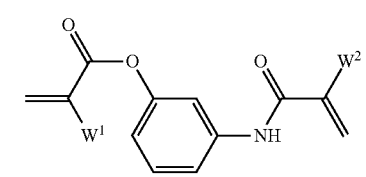
(5-12)

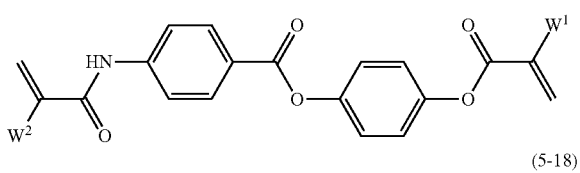
(5-16)

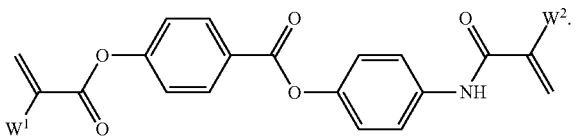
(5-18)

11. The liquid crystal composition according to claim 1, wherein the first monomer represented by the chemical formula (2) is a compound represented by one of the following chemical formulas (5-10), (5-12), (5-16), and (5-18); and the second monomer is a compound represented by the following chemical formula (11):

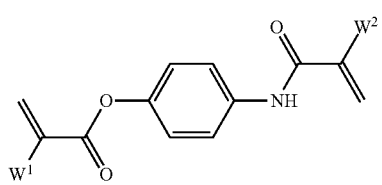
(5-10)

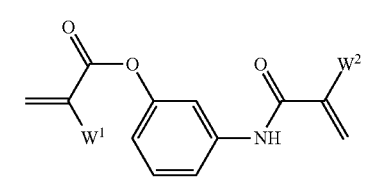
(5-12)

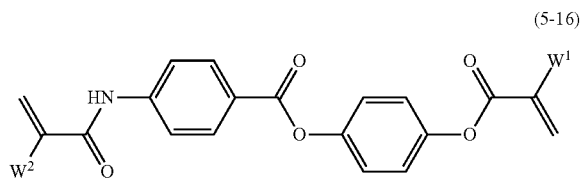
(5-16)

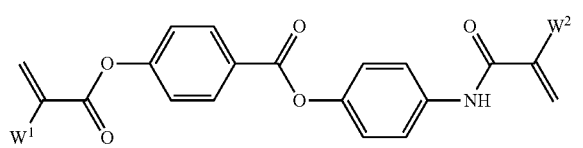
(5-18)

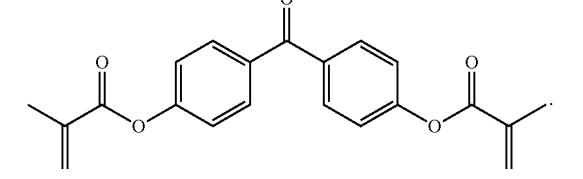
(11)

12. The liquid crystal composition according to claim 1, wherein the first monomer represented by the chemical formula (2) is a compound represented by one of the following chemical formulas (5-10), (5-12), (5-16), and (5-18); and the second monomer is a compound represented by the following chemical formula (12):

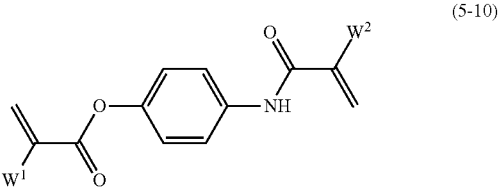
(5-10)

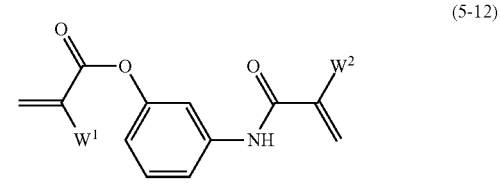
(5-12)

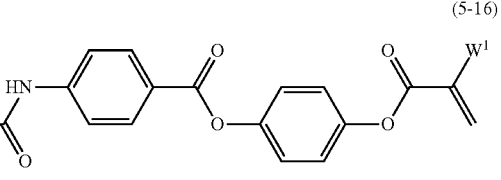
(5-16)

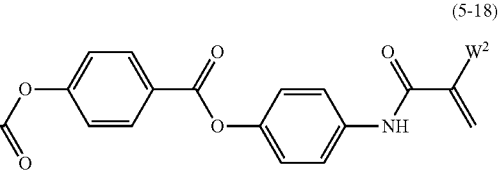
(5-18)

(12)

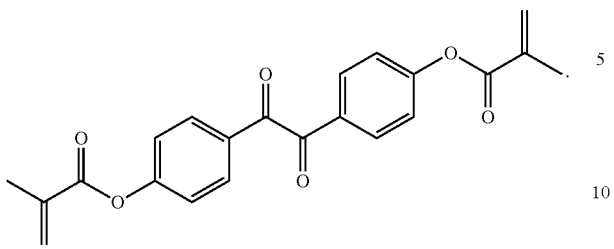

13. The liquid crystal composition according to claim 1, wherein
the first monomer represented by the chemical formula (2) is a compound represented by the following chemical formula (9); and
the second monomer is a compound represented by the following chemical formula (11):

(9)

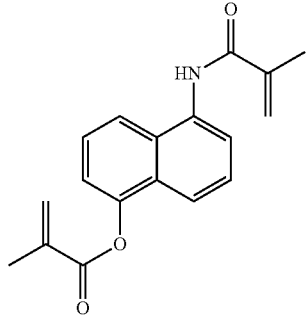

(11)

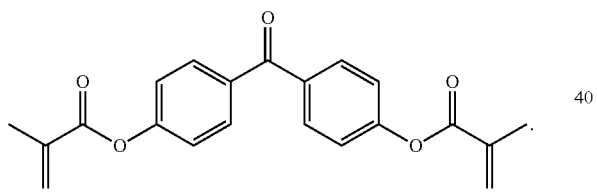

14. The liquid crystal composition according to claim 1, wherein
the first monomer represented by the chemical formula (2) is a compound represented by the following chemical formula (9); and
the second monomer is a compound represented by the following chemical formula (12):

(9)

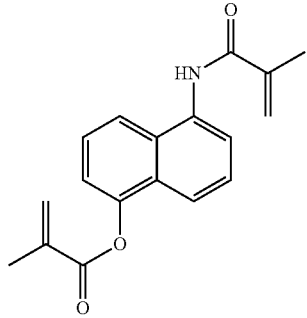

(12)

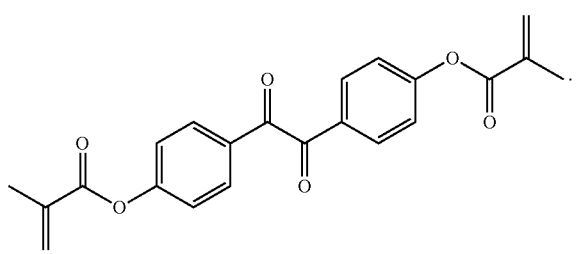

15. A liquid crystal display device comprising:
a pair of substrates;
a liquid crystal layer containing a liquid crystal material and sandwiched between the pair of the substrates; and
a polymer layer defined on at least one of the pair of substrates that controls alignment of liquid crystal molecules, the polymer layer being defined by polymerizing one or more kinds of monomers, the monomers including:
a first monomer represented by the following chemical formula (2); and
a second monomer being at least one of a compound represented by the following chemical formulas (6-1) to (6-8) and having a structure producing a radical by hydrogen abstraction reaction by light irradiation, and a compound represented by the following chemical formula (7) and having a structure producing a radical by self-cleavage reaction by light irradiation;

(2)

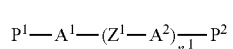

where, in the chemical formula (2):
$A^1$ denotes a divalent alicyclic, aromatic monocyclic, or condensed polycyclic hydrocarbon group;
$A^2$ denotes a phenylene group;
a —$CH_2$— group included in $A^1$ and $A^2$ may be substituted with an —O— or a —S— group unless neighboring each other;
a —CH= group included in $A^1$ and $A^2$ may be substituted with a —N= group unless neighboring each other;
a hydrogen atom included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;
$Z^1$ denotes —O—, —CO—, —COO—, —OCO—, —NRCO—, —CONR— groups, or a direct bond;
R denotes a hydrogen atom, or a straight alkyl or alkenyl group with 1 to 6 carbon atoms;
$P^1$ and $P^2$ each denote a radical polymerizable group, one of $P^1$ and $P^2$ is an acryloylamino or a methacryloy lamino group, and the other of P¹ and P² is an acryloyl or a methacryloyl group; and $n^1$ denotes 0 or 1,

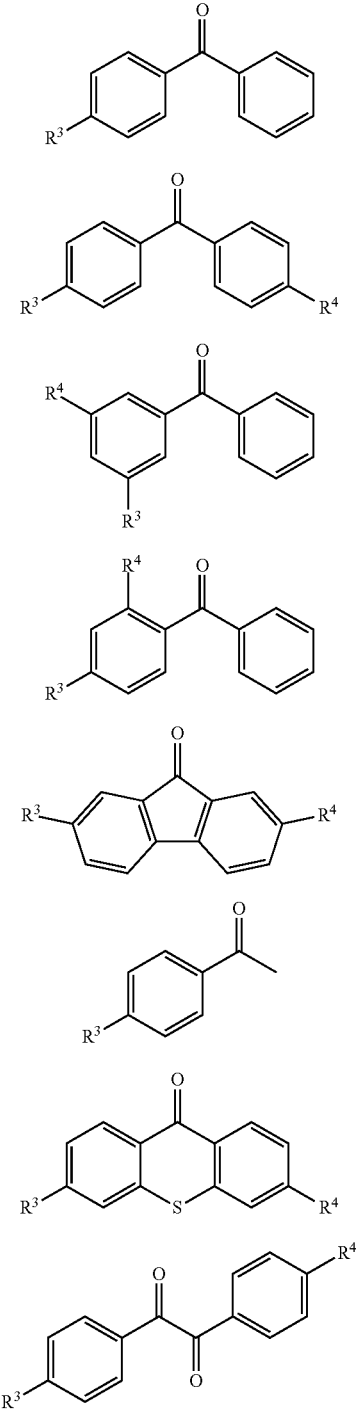

where, in the chemical formulas (6-1) to (6-8):
$R^3$ and $R^4$ may be the same or different, and denote a -$Sp^8$-P group, a hydrogen atom, a halogen atom, —CN, —NO$_2$, —NCO, —NCS, —OCN, —SCN, —SF$_5$, or a straight or branched alkyl or aralkyl with 1 to 12 carbon atoms, or phenyl group;

at least one of $R^3$ and $R^4$ contains a -$Sp^8$-P group;

P denotes a radical polymerizable group;

$Sp^8$ denotes a straight, branched or cyclic alkylene or alkyleneoxy group with 1 to 6 carbon atoms, or a direct bond;

in the case where at least one of $R^3$ and $R^4$ is an alkyl or aralkyl with 1 to 12 carbon atoms or phenyl group, a hydrogen atom included in $R^3$ and $R^4$ may be substituted with a fluorine atom, a chlorine atom, or a -$Sp^8$-P group; and a —CH$_2$— group included in $R^3$ and $R^4$ may be substituted with —O—, —S—, —NH—, —CO—, —COO—, —OCO—, —O—COO—, —OCH$_2$—, —CH$_2$O—, —SCH$_2$—, —CH$_2$S—, —N(CH$_3$)—, —N(C$_2$H$_5$)—, —N(C$_3$H$_7$)—, —N(C$_4$H$_9$)—, —CF$_2$O—, —OCF$_2$—, —CF$_2$S—, —SCF$_2$—, —N(CF$_3$)—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, or —OCO—CH═CH— group unless an oxygen atom, a sulfur atom, and a nitrogen atom neighbor one another,

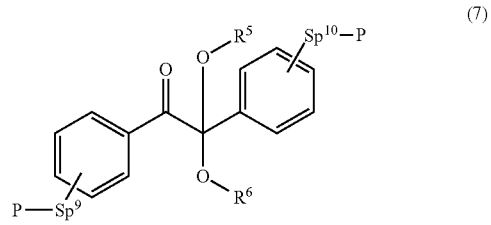

(7)

where, in the chemical formula (7):
$R^5$ denotes a straight or branched alkyl or alkenyl group with 1 to 4 carbon atoms;
$R^6$ denotes a straight or branched alkyl or alkenyl group with 1 to 4 carbon atoms;
P denotes the same or different radical polymerizable group;
$Sp^9$ denotes a straight, branched, or cyclic alkylene, alkyleneoxy, or alkylenecarbonyloxy group with 1 to 6 carbon atoms, or a direct bond; and
$Sp^{10}$ denotes a straight, branched, or cyclic alkylene, alkyleneoxy, or alkylenecarbonyloxy group with 1 to 6 carbon atoms, or a direct bond, wherein
the first monomer represented by the chemical formula (2) is a compound represented by one of the following chemical formulas (5-10), (5-12), (5-16), and (5-18):

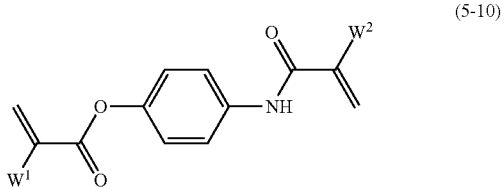

(5-10)

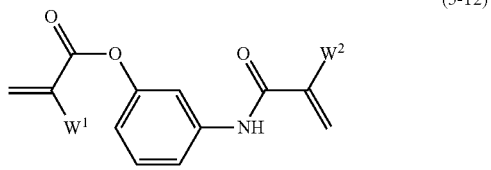

(5-12)

-continued (5-16)
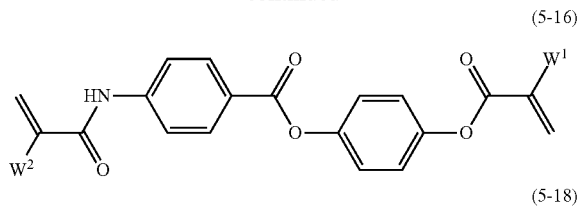

(5-18)
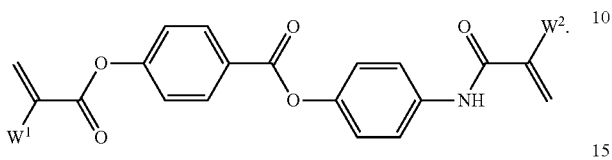

16. The liquid crystal display device according to claim 2, wherein the first monomer represented by the chemical formula (2) is a compound represented by one of the following chemical formulas (5-10), (5-12), (5-16), and (5-18); and the second monomer is a compound represented by the following chemical formula (11):

(5-10)
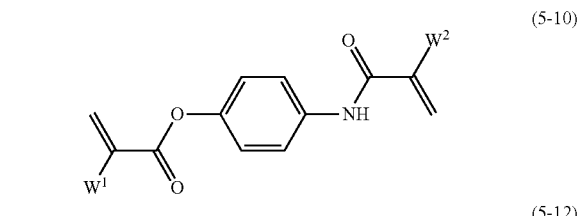

(5-12)
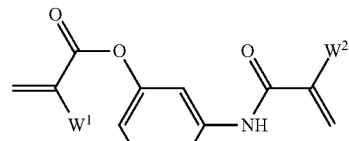

(5-16)
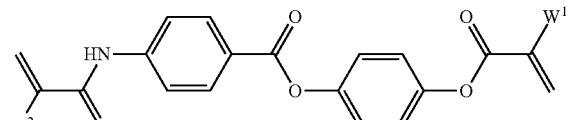

(5-18)
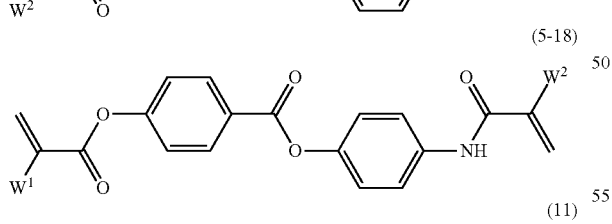

(11)
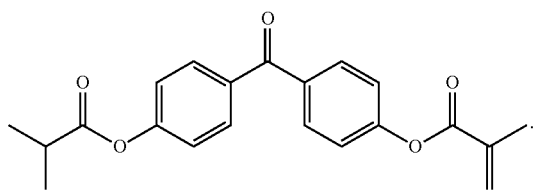

17. The liquid crystal display device according to claim 2, wherein the first monomer represented by the chemical formula (2) is a compound represented by one of the following chemical formulas (5-10), (5-12), (5-16), and (5-18); and the second monomer is a compound represented by the following chemical formula (12):

(5-10)
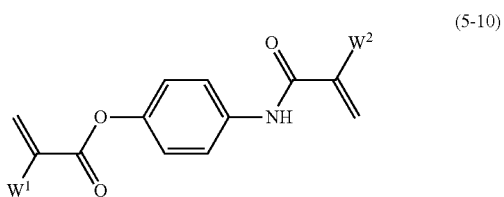

(5-12)
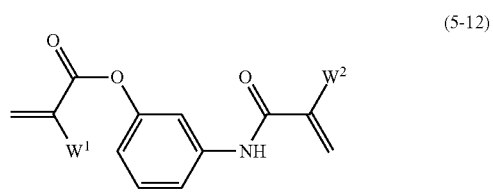

(5-16)
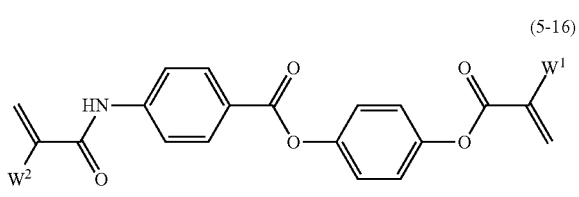

(5-18)
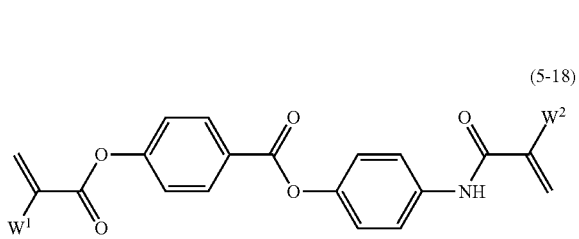

(12)

18. The liquid crystal display device according to claim 2, wherein the first monomer represented by the chemical formula (2) is a compound represented by the following chemical formula (9); and the second monomer is a compound represented by the following chemical formula (11):

(9)

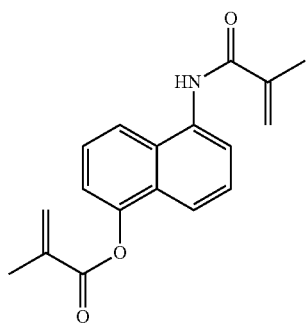

(11)

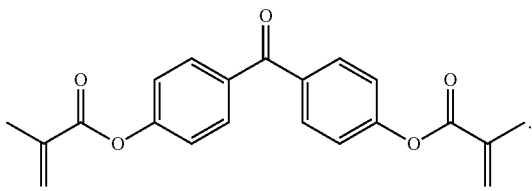

19. The liquid crystal display device according to claim 2, wherein
the first monomer represented by the chemical formula (2) is a compound represented by the following chemical formula (9); and
the second monomer is a compound represented by the following chemical formula (12):

(9)

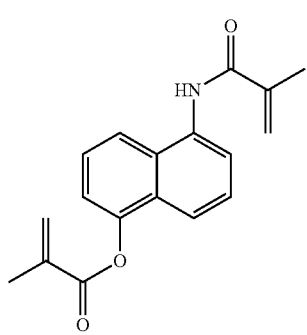

(12)

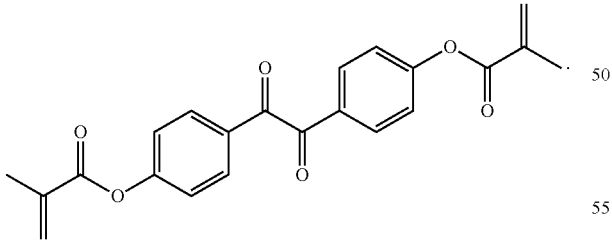

20. A production method for a liquid crystal display device comprising:
injecting a liquid crystal composition containing a liquid crystal material and one or more kinds of monomers between a pair of substrates; and
forming a polymer layer that controls alignment of liquid crystal molecules on the pair of substrates by irradiating the liquid crystal composition with light and thereby polymerizing the monomers, the monomers including:

a first monomer represented by the following chemical formula (2); and
a second monomer being at least one of a compound represented by the following chemical formulas (6-1) to (6-8) and having a structure producing a radical by hydrogen abstraction reaction by light irradiation, and a compound represented by the following chemical formula (7) and having a structure producing a radical by self-cleavage reaction by light irradiation;

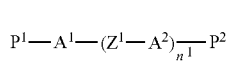

(2)

where, in the chemical formula (2):

$A^1$ denotes a divalent alicyclic, aromatic monocyclic, or condensed polycyclic hydrocarbon group;

$A^2$ denotes a phenylene group;

a —$CH_2$— group included in $A^1$ and $A^2$ may be substituted with an —O— or a —S— group unless neighboring each other;

a —CH= group included in $A^1$ and $A^2$ may be substituted with a —N= group unless neighboring each other;

a hydrogen atom included in $A^1$ and $A^2$ may be substituted with a fluorine atom, a chlorine atom, a —CN group, or a straight or branched alkyl, alkoxy, alkylcarbonyl, alkoxycarbonyl, or alkylcarbonyloxy group with 1 to 12 carbon atoms and further one or more of carbon atoms in these groups may be substituted with a silicon atom;

$Z^1$ denotes —O—, —CO—, —COO—, —OCO—, —NRCO—, —CONR— groups, or a direct bond;

R denotes a hydrogen atom, or a straight alkyl or alkenyl group with 1 to 6 carbon atoms;

$P^1$ and $P^2$ each denote a radical polymerizable group, one of $P^1$ and $P^2$ is an acryloylamino or a methacryloylamino group, and the other of $P^1$ and $P^2$ is an acryloyl or a methacryloyl group; and $n^1$ denotes 0 or 1, (6-1)

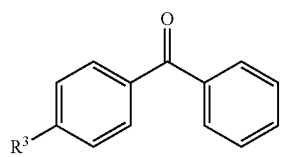

(6-2)

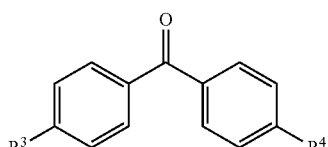

(6-3)

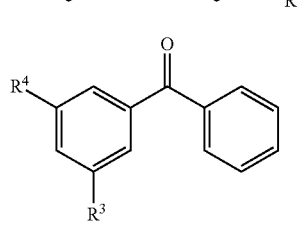

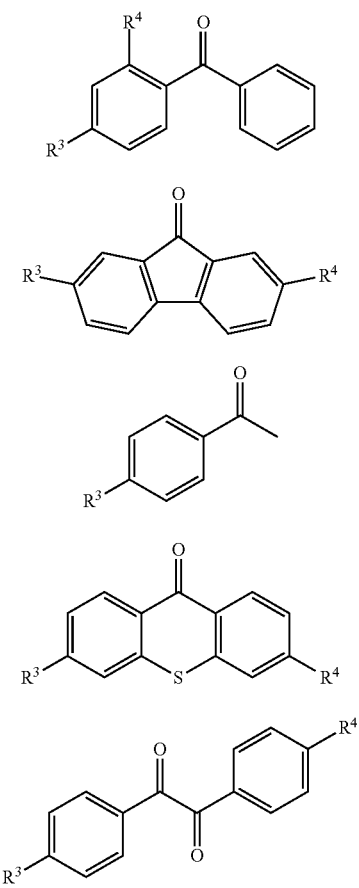

(6-4)

(6-5)

(6-6)

(6-7)

(6-8)

where, in the chemical formulas (6-1) to 6-8):
$R^3$ and $R^4$ may be the same or different, and denote a -$Sp^8$-P group, a hydrogen atom, a halogen atom, —CN, —$NO_2$, —NCO, —NCS, —OCN, —SCN, —$SF_5$, or a straight or branched alkyl or aralkyl with 1 to 12 carbon atoms, or phenyl group;

at least one of $R^3$ and $R^4$ contains a -$Sp^8$-P group;

P denotes a radical polymerizable group;

$Sp^8$ denotes a straight, branched or cyclic alkylene or alkyleneoxy group with 1 to 6 carbon atoms, or a direct bond;

in the case where at least one of $R^3$ and $R^4$ is an alkyl or aralkyl with 1 to 12 carbon atoms or phenyl group, a hydrogen atom included in $R^3$ and $R^4$ may be substituted with a fluorine atom, a chlorine atom, or a -$Sp^8$-P group; and a —$CH_2$— group included in $R^3$ and $R^4$ may be substituted with —O—, —S—, —NH—, —CO—, —COO—, —OCO—, —O—COO—, —$OCH_2$—, —$CH_2O$—, —$SCH_2$—, —$CH_2S$—, —$N(CH_3)$—, —$N(C_2H_5)$—, —$N(C_3H_7)$—, —$N(C_4H_9)$—, —$CF_2O$—, —$OCF_2$—, —$CF_2S$—, —$SCF_2$—, —$N(CF_3)$—, —$CH_2CH_2$—, —$CF_2CH_2$—, —$CH_2CF_2$—, —$CF_2CF_2$—, —CH═CH—, —CF═CF—, —C≡C—, —CH═CH—COO—, or —OCO—CH═CH— group unless an oxygen atom, a sulfur atom, and a nitrogen atom neighbor one another,

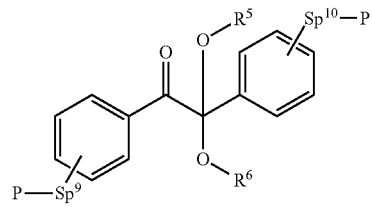

(7)

where, in the chemical formula (7):
$R^5$ denotes a straight or branched alkyl or alkenyl group with 1 to 4 carbon atoms;
$R^6$ denotes a straight or branched alkyl or alkenyl group with 1 to 4 carbon atoms;
P denotes the same or different radical polymerizable group;
$Sp^9$ denotes a straight, branched, or cyclic alkylene, alkyleneoxy, or alkylenecarbonyloxy group with 1 to 6 carbon atoms, or a direct bond; and
$Sp^{10}$ denotes a straight, branched, or cyclic alkylene, alkyleneoxy, or alkylenecarbonyloxy group with 1 to 6 carbon atoms, or a direct bond, wherein
the first monomer represented by the chemical formula (2) is a compound represented by one of the following chemical formulas (5-10), (5-12), (5-16), and (5-18):

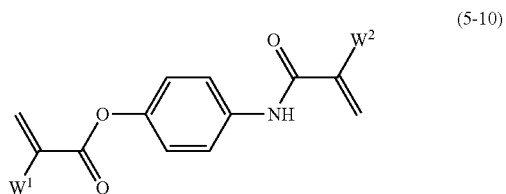

(5-10)

(5-12)

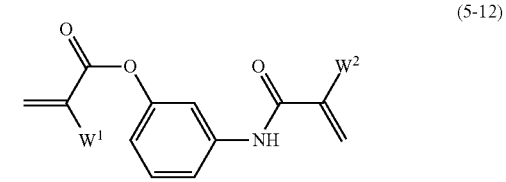

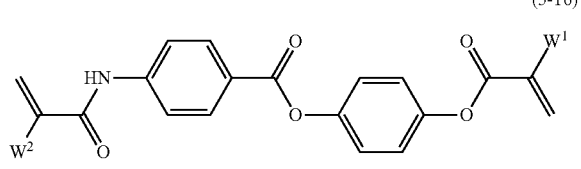

(5-16)

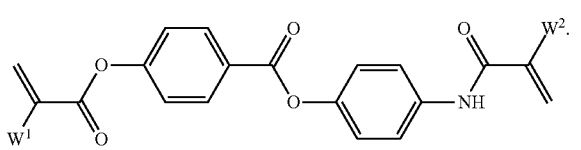

(5-18)

21. The production method for a liquid crystal display device according to claim 3, wherein
the first monomer represented by the chemical formula (2) is a compound represented by one of the following chemical formulas (5-10), (5-12), (5-16), and (5-18); and
the second monomer is a compound represented by the following chemical formula (11):

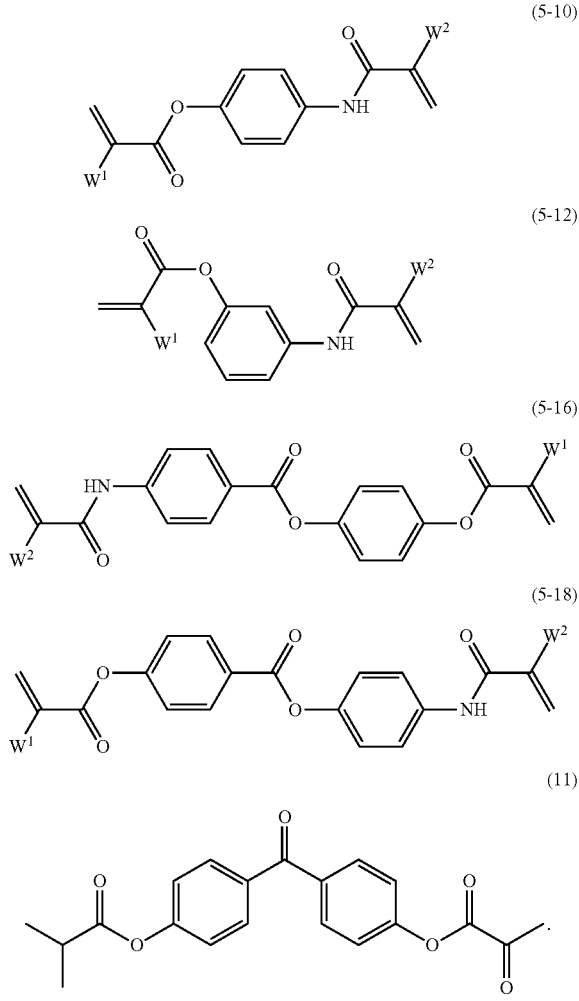

22. The production method for a liquid crystal display device according to claim 3, wherein the first monomer represented by the chemical formula (2) is a compound represented by one of the following chemical formulas (5-10), (5-12), (5-16), and (5-18); and the second monomer is a compound represented by the following chemical formula (12):

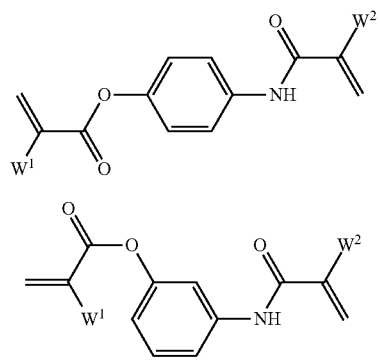

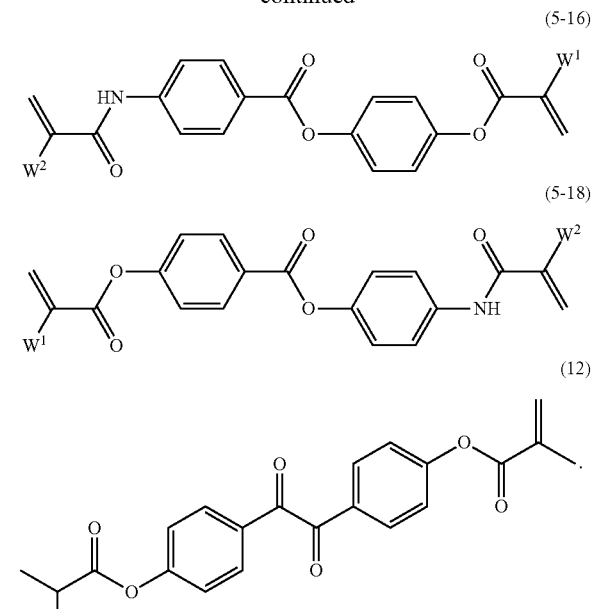

23. The production method for a liquid crystal display device according to claim 3, wherein the first monomer represented by the chemical formula (2) is a compound represented by the following chemical formula (9); and the second monomer is a compound represented by the following chemical formula (11):

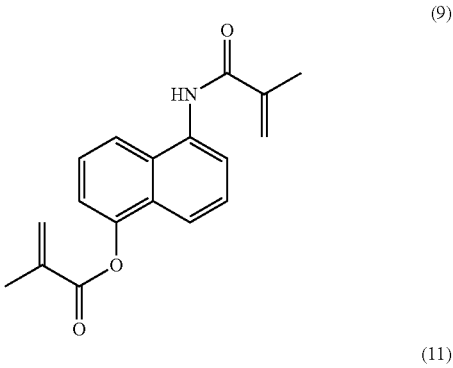

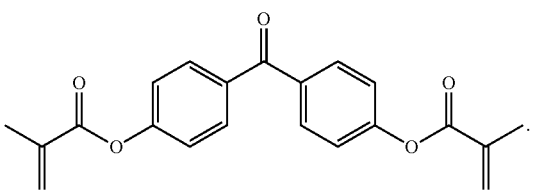

24. The production method for a liquid crystal display device according to claim 3, wherein the first monomer represented by the chemical formula (2) is a compound represented by the following chemical formula (9); and the second monomer is a compound represented by the following chemical formula (12):

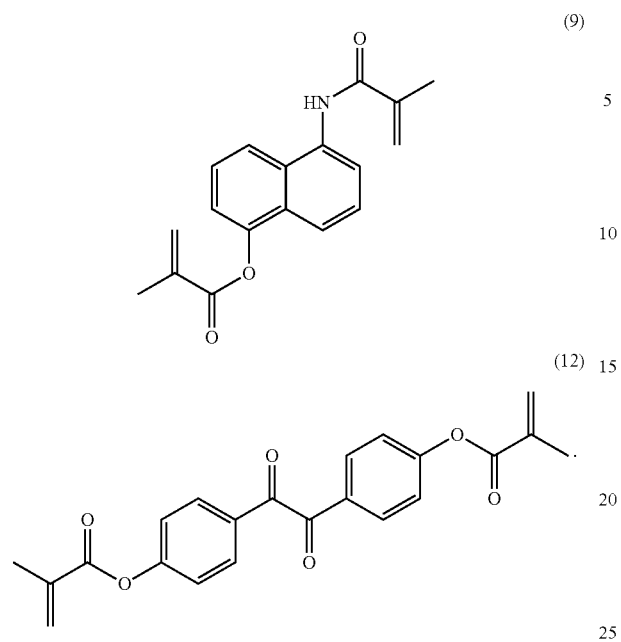
* * * * *